US010059907B2

(12) United States Patent
Ribaut et al.

(10) Patent No.: US 10,059,907 B2
(45) Date of Patent: Aug. 28, 2018

(54) MICROCAPSULES

(71) Applicant: TAKASAGO INTERNATIONAL CORPORATION, Tokyo (JP)

(72) Inventors: Tiphaine Ribaut, Paris (FR); Jonathan Warr, Paris (FR); Stuart Fraser, Cheshire (GB); Olivier Anthony, Paris (FR)

(73) Assignee: TAKASAGO INTERNATIONAL CORPORATION, Ota-ku, Tokyo (JP)

( * ) Notice: Subject to any disclaimer, the term of this patent is extended or adjusted under 35 U.S.C. 154(b) by 0 days.

(21) Appl. No.: 14/908,278

(22) PCT Filed: Jul. 28, 2014

(86) PCT No.: PCT/JP2014/070409
§ 371 (c)(1),
(2) Date: Jan. 28, 2016

(87) PCT Pub. No.: WO2015/016368
PCT Pub. Date: Feb. 5, 2015

(65) Prior Publication Data
US 2016/0168507 A1  Jun. 16, 2016

(30) Foreign Application Priority Data
Jul. 29, 2013  (EP) .................................... 13306093

(51) Int. Cl.
| C11B 9/00 | (2006.01) |
| A61K 8/11 | (2006.01) |
| A61Q 13/00 | (2006.01) |
| C11D 3/50 | (2006.01) |
| B01J 13/14 | (2006.01) |
| A61K 8/81 | (2006.01) |

(52) U.S. Cl.
CPC .................. C11B 9/00 (2013.01); A61K 8/11 (2013.01); A61K 8/817 (2013.01); A61Q 13/00 (2013.01); B01J 13/14 (2013.01); C11D 3/505 (2013.01); A61K 2800/412 (2013.01); A61K 2800/56 (2013.01)

(58) Field of Classification Search
CPC ...... A61K 2800/56; A61K 8/11; A61Q 13/00; B01J 13/14
See application file for complete search history.

(56) References Cited

U.S. PATENT DOCUMENTS

| 6,200,681 | B1 | 3/2001 | Jahns et al. | |
| 6,337,089 | B1* | 1/2002 | Yoshioka | ................. A61K 8/11 424/400 |
| 2003/0118822 | A1 | 6/2003 | Jahns et al. | |
| 2003/0125222 | A1 | 7/2003 | Jahns et al. | |
| 2004/0157057 | A1 | 8/2004 | Tasaki et al. | |
| 2012/0112122 | A1 | 5/2012 | Jung et al. | |
| 2016/0206522 | A1* | 7/2016 | Ribaut | ............... C11D 17/0039 |

FOREIGN PATENT DOCUMENTS

| CN | 102108106 A | | 6/2011 | |
| DE | 19749731 A1 | | 5/1999 | |
| EP | 1321182 A1 | | 6/2003 | |
| JP | 6-254380 A | | 9/1994 | |
| JP | 2002-363537 A | | 12/2002 | |
| WO | 01/049817 A2 | | 7/2001 | |
| WO | 2011/004006 A2 | | 1/2011 | |
| WO | WO 2011/004006 | * | 1/2011 | ................ C08F 2/44 |
| WO | WO2013/078551 | * | 6/2013 | .............. B01J 13/06 |

OTHER PUBLICATIONS

International Search Report for PCT/JP2014/070409 dated Oct. 14, 2014 [PCT/ISA/210].
Written Opinion for PCT/JP2014/070409 dated Oct. 14, 2014 [PCT/ISA/237].
Communication dated Dec. 12, 2016, issued by the Intellectual Property Office of the People's Republic of China in counterpart Chinese Patent Application No. 201480043190.3.
Communication dated Aug. 1, 2017, issued by the Intellectual Property Office of the People's Republic of China in counterpart Chinese Patent Application No. 201480043190.3.

* cited by examiner

*Primary Examiner* — Anna R Falkowitz
(74) *Attorney, Agent, or Firm* — Sughrue Mion, PLLC

(57) ABSTRACT

A novel microcapsule which is endowed for example with reduced leakage of encapsulated materials. The microcapsule contains one or more fragrances and is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

18 Claims, No Drawings

MICROCAPSULES

TECHNICAL FIELD

The present disclosure discloses a microcapsule which comprises a perfume composition enclosed within a polymeric shell, a process for the manufacture of that microcapsule as well as non-ingestible consumer products (such as household cleaners, laundry products, personal care products and cosmetic products) containing that microcapsule.

BACKGROUND ART

Microencapsulation through free radical polymerization entails the preliminary formation of an emulsion wherein a continuous, typically aqueous-based, phase disperses an internal, hydrophobic phase to be encapsulated. In suspension free radical polymerization the formation of the microcapsule polymeric wall relies on growing polymer chains migrating from the internal phase of the emulsion to the interface between the two phases. Once this process is complete, a dispersion of microcapsules encapsulating the internal phase is typically obtained.

SUMMARY OF INVENTION

Technical Solution

When performing this process it would be desirable to reduce the formation of (unwanted) latex particles and achieve an effective formation of the capsule shell. Both aspects may be particularly challenging when working with fragrances due to their typically complex chemical nature.

The present disclosure provides a microcapsule containing one or more fragrances which is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

Solution to Problem

The present disclosure discloses a microcapsule which comprises a perfume composition enclosed within a polymeric shell. The microcapsule is endowed with advantageous properties such as reduced leakage of the fragrance for example upon storage and especially upon storage in a liquid medium. The instant disclosure also discloses certain microcapsules which display pH-independent shell properties. This means for example that certain microcapsules may display satisfactory shell properties in acid (e.g. from pH 2) and alkaline conditions (e.g. up to pH 12) as can be found in many liquid household, laundry personal care and cosmetic products, such as fabric conditioners and antiperspirants (acidic pH) or liquid laundry detergents and hard surface cleaners (alkaline pH). The instant disclosure also discloses a dispersion of fragrance-containing microcapsules as presently defined, wherein the amount of latex particles (i.e. small solid polymer beads) is particularly low. The instant disclosure also discloses a simple and effective suspension free-radical polymerization process for the manufacture of a microcapsule or dispersion as presently defined. The instant disclosure also discloses a technical solution to maintain appropriate homogeneity and viscosity of forming microcapsule dispersion while suspension free-radical polymerization progresses. The instant disclosure also discloses a non-edible consumer goods product, a laundry product, a personal care product or a cosmetic product containing a microcapsule or a dispersion of microcapsules as presently defined. In particular, the present disclosure discloses the following points:

1. A microcapsule comprising a perfume composition enclosed within a polymeric shell, wherein:
   the perfume composition includes a fragrance,
   the polymeric shell includes solid colloidal particles having an average primary particle size comprised between 5 nm (nanometer) and 1 μm (micrometer),
   the polymeric shell further includes in polymerized form a blend including:
   i) between 20% and 75% by weight over the combined weight of compounds (I) to (III) in the blend of a compound (I) which is a monoethylenically unsaturated monomer and/or dimethyldiallyl ammonium chloride (DMDAAC),
   ii) between 20% and 70% by weight over the combined weight of compounds (I) to (III) in the blend of a compound (II) which is a polyethylenically unsaturated monomer selected from the group consisting of a $C_2$-$C_{24}$ alkyl di- or polyester of (meth)acrylic acid, a $C_2$-$C_{24}$ alkyl di- or polyamide of (meth)acrylic acid and mixtures thereof, and
   iii) between 0.01% and 10% by weight over the combined weight of compounds (I) to (III) in the blend of a compound (III) which is a silane compound.

2. A microcapsule comprising a perfume composition enclosed within a polymeric shell, wherein:
   the perfume composition includes a fragrance,
   the polymeric shell includes solid colloidal particles having an average primary particle size comprised between 5 nm and 1 μm,
   the polymeric shell further includes in polymerized form a blend including:
   i) between 20% and 75% by weight over the combined weight of compounds (I) to (III) in the blend of a compound (I) which is a monoethylenically unsaturated monomer and/or dimethyldiallyl ammonium chloride (DMDAAC),
   ii) between 20% and 70% by weight over the combined weight of compounds (I) to (III) in the blend of a compound (II) which is a polyethylenically unsaturated monomer selected from the group consisting of a $C_2$-$C_{24}$ alkyl di- or polyester of (meth)acrylic acid, a $C_2$-$C_{24}$ alkyl di- or polyamide of (meth)acrylic acid and mixtures thereof, and
   iii) between 0.01% and 10% by weight over the combined weight of compounds (I) to (III) in the blend of a compound (III) which is a silane compound, wherein the compound (II) is such that the microcapsule provides for a fragrance leakage of less than about 35% when tested upon storage for 4 weeks at 40° C. in a test liquid base, according to a leakage test method, when the microcapsule is prepared according to a leakage test manufacturing procedure, and the microcapsule encapsulates fragrance no. 5, the test liquid base, the leakage test method, the leakage test manufacturing procedure and the fragrance no. 5 being as defined in the examples.

3. A microcapsule comprising a perfume composition enclosed within a polymeric shell, wherein:
   the perfume composition includes a fragrance,
   the polymeric shell includes solid colloidal particles having an average primary particle size comprised between 5 nm and 1 μm, the polymeric shell further includes in polymerized form a blend including:
  i) between 20% and 75% by weight over the combined weight of compounds (I) to (III) in the blend of a compound (I) which is a monoethylenically unsaturated monomer and/or dimethyldiallyl ammonium chloride (DMDAAC),
  ii) between 20% and 70% by weight over the combined weight of compounds (I) to (III) in the blend of a compound (II) which is a polyethylenically unsaturated monomer selected from the group consisting of a $C_2$-$C_{24}$ alkyl di- or polyester of (meth)acrylic acid, a $C_2$-$C_{24}$ alkyl di- or polyamide of (meth)acrylic acid and mixtures thereof, and which:
    A1. contains two or more (meth)acrylate ester groups or two or more (meth)acrylate amide groups per monomer, and
    B1. has a molecular weight which, once divided by the number of (meth)acrylate ester or amide groups, gives a value of more than 85 and lower than 135; and
  iii) between 0.01% and 10% by weight over the combined weight of compounds (I) to (III) in the blend of a compound (III) which is a silane compound.

4. The microcapsule according to any one of points 1 to 3, wherein the compound (I) is selected from the group consisting of methacrylic acid, methyl methacrylate, ethyl methacrylate, isopropyl methacrylate, 2-hydroxyethyl methacrylate, 2-hydroxypropyl methacrylate, 3-hydroxypropyl methacrylate, and mixtures thereof.

5. The microcapsule according to any one of points 1 to 3, wherein the compound (I) is a combination of:
  ia) between 50% and 100% by weight over the weight of the combination of a neutral monomethacrylate monomer (Ia) having a solubility in water at pH 7 and 20° C. equal to, or more than 2 g/100 ml,
  ib) between 0% and 50% by weight over the weight of the combination of another neutral monoethylenically unsaturated monomer (Ib), and
  ic) between 0% and 15% by weight over the weight of the combination of a ionized or ionizable monoethylenically unsaturated monomer (Ic).

6. The microcapsule according to point 5, wherein the neutral monomethacrylate monomer (Ia) is selected from the group consisting of 2-hydroxyethyl methacrylate, 2-hydroxypropyl methacrylate, 3-hydroxypropyl methacrylate, glycidyl methacrylate, poly(ethylene glycol) methyl ether methacrylate and mixtures thereof.

7. The microcapsule according to any one of points 1 to 6, wherein the compound (II) is a di- or polyester resulting from the esterification of (meth)acrylic acid with a linear or branched polyhydric $C_2$-$C_{24}$ alcohol and/or $C_2$-$C_{24}$ polyethylene glycols.

8. The microcapsule according to point 7, wherein the compound (II) comprises one or more of 1,4-butylene glycol dimethacrylate, ethylene glycol dimethacrylate and 1,3-propylene glycol dimethacrylate.

9. The microcapsule according to any one of points 1 to 8, wherein the compound (III) comprises methacryloxypropyltrimethoxysilane and/or methacryloxypropyltriethoxysilane.

10. A water-based dispersion comprising the microcapsule as defined according to any one of points 1 to 9.

11. A water-based dispersion as defined in point 10, which is substantially free of latex particles.

12. A product comprising the microcapsule as defined according to any one of points 1 to 9 or the water-based dispersion as defined in point 10 or 11, and which is a non-edible consumer goods product, a household cleaner or laundry product, a personal care product or a cosmetic product.

13. A process for the manufacture of the microcapsule as defined in any one of points 1 to 9, which comprises the following steps:
  a) providing an oil-in-water emulsion having an oil phase and a water phase, said oil-in-water emulsion being obtainable by mixing:
    colloidal silica particles having an average primary particle size comprised between 5 nm and 1 µm,
    an oil soluble polymerization initiator,
    a perfume composition including a fragrance,
    the blend as defined in any one of points 1 to 9, and
    a protective colloid,
  b) triggering polymerization within the oil phase of the oil-in-water emulsion obtained in step a),
  c) letting the polymerization propagate thereby obtaining microcapsules.

14. Use of a combination of solid colloidal particles having an average primary particle size comprised between 5 nm and 1 µm and a silane compound to reduce latex particles formation in a suspension free radical polymerization process for the manufacture of a microcapsule containing a perfume composition, wherein the perfume composition includes a fragrance.

15. Use of a combination of solid colloidal particles having an average primary particle size comprised between 5 nm and 1 µm and a silane compound to reduce leakage of a microcapsule containing a perfume composition, wherein the perfume composition includes a fragrance.

16. Use of a combination of solid colloidal particles having an average primary particle size comprised between 5 nm and 1 µm and a silane compound to microencapsulate a perfume composition including a fragrance.

Advantageous Effects of Invention

The microcapsule containing one or more fragrances is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

DESCRIPTION OF EMBODIMENTS

Unless otherwise stated, all percentages are weight percentages.

Unless otherwise indicated "an" or "a" means one or more.

Unless otherwise indicated, all chemical terms have the meanings defined by the IUPAC Compendium of Chemical Terminology $2^{nd}$ Edition Compiled by A D McNaught and A Wilkinson Blackwell Scientific Publications Oxford 1997 and IUPAC Nomenclature of Organic Chemistry, published by Blackwell Scientific Publications Oxford 1993 ISBN 0632034882.

Unless otherwise indicated, the language "blend", "a blend" or "monomer blend" refers to the blend including compounds (I) to (III).

Unless otherwise indicated, compounds referred to as monomer(s) are monomers which can be polymerized by free radical polymerization.

Unless otherwise indicated, references to "latex particles" or "latex particles formation" are to be understood to refer to latex particles which form during the polymerization in the aqueous phase of the emulsion. Typically latex particles have a size in the range from 5 nm to 5 μm in diameter.

Unless otherwise indicated "(meth)acrylate" (or "(meth)acrylic") means methacrylate (or methacrylic) and/or acrylate (or acrylic). For example, it means methacrylate (or methacrylic). For example it means acrylate (or acrylic). For example it means methacrylate (or methacrylic) and acrylate (or acrylic).

Unless otherwise indicated, methacrylate and acrylate ester groups are groups having molecular weight of 85 and 71 mass units, respectively, and the following structures

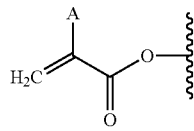

wherein A is $CH_3$ for a methacrylate ester group or A is H for an acrylate ester group.

Unless otherwise indicated, methacrylate or acrylate amide groups are groups having molecular weight of 84 and 70 mass units, respectively, and the following structures

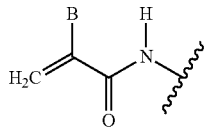

wherein B is $CH_3$ for a methacrylate amide group or B is H for an acrylate amide group.

Unless otherwise indicated, room temperature is 20° C.

Certain substances, notably perfumery molecules, may exist as distinct isomers (or as mixture of distinct isomers). Hereinafter, they may be identified also by means of their CAS number. In these cases, the CAS number of a single isomer is reported. However, and unless otherwise indicated, the reference shall be understood to cover all existing isomers. For substances which have several isomers regardless of whether isomeric purity is specified, the use of a CAS number of any isomer or a collective CAS number should cover all possible isomers of that particular substance.

The present disclosure discloses a microcapsule which comprises, such as consists of, a perfume composition enclosed within a polymeric shell.

Methods of preparation of perfume-containing microcapsules are described for example in MICROENCAPSULATION: Methods and Industrial Applications Edited by Benita and Simon (Marcel Dekker, Inc. 1996) and in Kirk Othmer Encyclopedia of Chemical Technology Microencapsulation by C. Thies. Microcapsules obtainable by free radical polymerization are well known to those working in the field of e.g. encapsulated perfumes and are structurally (and dimensionally) different from other types of capsules such as conventional seamless soft capsules or two-piece hard capsules used e.g. in pharmacy to orally or rectally administrate substances to a subject.

The microcapsules presently disclosed are not intended for oral or rectal administration to human or animal subjects.

A microcapsule as presently disclosed may have a shell thickness comprised between about 100 nm and 800 nm, such as between about 200 nm and 700 nm, for example between about 300 nm and 600 nm.

A microcapsule as presently disclosed may have a perfume composition-to-shell weight ratio which is comprised between 50:1 and 1:1, such as between 30:1 and 1:1, or between 20:1 and 1:1, for example between 10:1 and 1:1.

The microcapsule presently disclosed may be substantially spherical.

The microcapsule presently disclosed may have an average particle size (median volume particle size D(v; 0.5) value) equal to or greater than 7.5 microns (7.5 μm), for example equal to or greater than 10 μm, such as equal to or greater than 15 μm, or equal to or greater than 20 μm, for example equal to or greater than 25 μm. The microcapsule presently disclosed may have an average particle size equal to or less than 60 microns (60 μm), for example equal to or less than 50 μm, such as equal to or less than 45 μm, for example equal to or less than 40 μm. The microcapsule presently disclosed may have an average particle size comprised between 7.5 microns (7.5 μm) and 60 microns (60 μm), or between 7.5 μm and 50 μm, or between 10 μm and 50 μm, or between 7.5 μm and 45 μm, or between 10 μm and 45 μm, or between 15 μm and 45 μm, or between 15 μm and 40 μm, or between 20 μm and 45 μm, or between 25 μm and 45 μm, or between 25 μm and 40 μm, or between 25 μm and 35 μm.

Microcapsules obtainable by free-radical polymerization have typically quite small (e.g. less than about 7 microns) average particle sizes. This might be due to a technical belief that this size better copes with an efficient polymerization, thus leading to capsules with better properties. At the same time, it was also believed that average particle size did not have a significant impact on final capsule leakage. The experimental results obtained by the present Applicant showed however that no significant issues with polymerization are met when targeting larger sizes and that larger average particle sizes may bring about an advantage in terms of leakage. If microcapsules with dimensions which do not make them visible to the naked eye when deposited on a black surface are desired, then it is recommendable to target an average particle size of less than e.g. 70 microns.

The preferred technique used in the present disclosure to measure the microcapsule average particle size is light scattering using for example a Horiba® or a Malvern® Laser scattering particle Size Distribution analyzer or an equivalent instrument working on the principle of low angle laser light scattering (LALLS) following the general guidelines set out in ISO 13320 "Particle Size Analysis—Laser Diffraction Methods".

The microcapsule polymeric shell comprises solid colloidal particles (also known as particulate colloids) having an average primary particle size comprised between 5 nm and 1 μm as measured for example through dynamic light scattering. Free radical polymerization for microcapsule preparation generally includes the initial formation of an oil-in-water emulsion. Particulate colloids allow obtaining Pickering oil-in-water emulsions stabilized by limited coalescence. The process of formation of Pickering emulsions is known. It is discussed for example in Whitesides and Ross, J. Interface Colloid Sci. 196, 48-59(1995).

Examples of materials which can be suitably used in the form of solid colloidal particles in the microcapsules presently disclosed are silica, quartz, glass, aluminum (AlO(OH)), alumino-silicates (e.g. clays), silicon, copper, tin (SnO), talc, inorganic oxides or hydroxides (e.g. $Fe_2O_3$, TiO$_2$, Cr$_2$O$_3$), steel, iron, asbestos, nickel, zinc, lead, marble, chalk (CaCO$_3$), gypsum (CaSO$_4$), barytes (e.g. BaSO$_4$), graphite and carbon black. Preferred materials are silica, alumino-silicates and inorganic oxides or hydroxides. Silica is a highly preferred material.

Solid colloidal particles suitable for the present disclosure may or may not be surface modified. Surface modification may either impart the ability to materials to partition to the interface of water and oil phases or it may improve the compatibility between the materials and the microcapsule polymeric shell. Examples of surface modification include chemical treatments to increase or decrease particles hydrophobicity. Alternatively, surface modifying agents can be adsorbed onto particles surface to impart appropriate surface active properties. Alternatively, particles may be modified by means of coupling agents which improve the compatibility between the materials and the microcapsule polymeric shell. Techniques to modify particle surfaces are discussed for example in "Nanoparticle Technology handbook" 1$^{st}$ edition, year 2007, Application 41 (pages 593-596) "Surface modification of inorganic nanoparticles by organic functional groups". Modified (as well as non-modified) solid colloidal particles are commercially available.

Examples of suitable colloidal silicas may be dry fumed silicas (such as commercially available in the Aerosil® range from Evonik®) or aqueous colloidal silica dispersions (such as those commercially available in the Ludox® range from Du Pont®). Dry silica particles may be fumed silica particles or condensed silica particles. Fumed silicas are particularly adapted for stabilizing emulsions with droplet sizes in the range of 10 µm to 100 µm. For larger droplets, colloidal silicas might be more appropriate. Suitable grades of fumed silica are Aerosil® 200 (a hydrophilic fumed silica with a specific surface area of 200 m$^2$/g) and Aerosil® R816 having a BET surface area of 190±20 m$^2$/g and an average primary particle size of about 12 nm, both available from Evonik®.

Amounts of solid colloidal particles may be comprised between 0.025% and 10%, such as between 0.05% and 7.5%, for example between 0.1% and 5%, such as between 0.2% and 3%, or between 0.3% and 2%, or between 0.3% and 1.2%, such as 0.6% by weight over the weight of a dried slurry.

The use of solid colloidal particles alone may lead to a non-fully satisfactory microcapsule shell. The combined use of solid colloidal particles and a silane compound as presently disclosed may overcome this effect and permit to achieve a high quality microcapsule shell even when microencapsulating fragrances that may inhibit the polymerization. In turn, this may finally impinge on the leakage of the final microcapsule.

Compound (I) is preferably a monoethylenically unsaturated monomer.

Suitable examples of compound (I) are:
a) C$_3$-C$_6$ monoethylenically unsaturated mono- or poly carboxylic acids,
b) amides of C$_3$-C$_6$ monoethylenically unsaturated mono- or poly carboxylic acids;
c) optionally mono- or polysubstituted C$_1$-C$_{24}$ linear or branched alkyl esters of C$_3$-C$_6$ monoethylenically unsaturated mono- or poly carboxylic acids, and
d) optionally mono- or polysubstituted C$_3$-C$_6$ cycloalkyl esters of C$_3$-C$_6$ monoethylenically unsaturated mono- or poly carboxylic acids,
wherein optional substituents are selected from the group consisting of —OH, —OR, —C(O)R, —NH$_2$, —NHR, —NR$_2$, —NR$_3^+$, —C$_5$-C$_6$ aromatic or heteroaromatic rings, and C$_3$-C$_{10}$ cyclo- or heterocyclic alkyl,
wherein R is C$_1$-C$_4$ alkyl. The carboxylic acid is preferably a monocarboxylic acid such as methacrylic acid.

For example, compound (I) is selected from acrylic acid, methacrylic acid, maleic acid, itaconic acid, 2-(diethylamino)ethyl methacrylate, dimethylaminoethyl methacrylate, 2-(tert-butylamino)ethyl methacrylate, N-[3-(dimethylamino)propyl]methacrylamide, 3-trimethylammonium propyl methacrylamide chloride, methyl methacrylate, ethyl methacrylate, n-propyl methacrylate, isopropyl methacrylate, tert-butyl methacrylate, isobutyl methacrylate, n-butyl methacrylate, methacrylamide, benzyl methacrylate, isobornyl methacrylate, cyclohexyl methacrylate, tetrahydrofuryl methacrylate, glycidyl methacrylate, 2-hydroxyethyl methacrylate, 2-hydroxypropyl methacrylate, 3-hydroxypropyl methacrylate, poly(ethylene glycol) methyl ether methacrylate, 2-ethyl(2-oxoimidazolidin-1-yl)methacrylate, acryloxyethyltrimethyl ammonium chloride, methacryloxyethyltrimethyl ammonium chloride and mixtures thereof.

Compound (I) may be selected from methacrylic acid, methyl methacrylate, ethyl methacrylate, isopropyl methacrylate, 2-hydroxyethyl methacrylate, 2- or 3-hydroxypropyl methacrylate and mixtures thereof, for example methacrylic acid, methyl methacrylate, ethyl methacrylate and mixtures thereof.

Compound (I) may be a combination of methacrylic acid and methyl and/or ethyl methacrylate. The combination may be used in an amount comprised between 30% and 60%, for example between 35% and 60% by weight over the combined weight of compounds (I) to (III) in the blend. In the combination, methacrylic acid may be present between 35% and 50%, such as between 45 and 47%, by weight, and methyl or ethyl methacrylate between 0% and 15%, such as between 0 and 8%, by weight over the combined weight of compounds (I) to (III) in the blend.

Advantageously, compound (I) is a monomethacrylate unsaturated monomer meaning that it contains one single methacrylate ester group. In effect, methacrylates proved to be less susceptible than acrylates to hydrolysis on prolonged exposure to acidic or alkaline pH and elevated storage temperatures. Hence, it may be advantageous that compound (I) does not contain acrylic acid derivatives such as C$_1$-C$_{24}$ alkyl or C$_3$-C$_6$ cycloalkyl esters or amides of acrylic acid.

In one embodiment, the blend includes for example between 30% and 60%, for example between 35% and 60% by weight over the combined weight of compounds (I) and (III) in the blend of a compound (I) which is a combination of:
ia) between 50% and 100%, such as between 60% and 100%, for example between 70% and 100% by weight over the weight of the combination of a neutral monomethacrylate monomer (Ia) having a solubility in water at 20° C. equal to, or more than 2 g/100 ml,
ib) between 0% and 50%, such as between 0% and 40%, for example between 0% and 30% by weight over the weight of the combination of another neutral monoethylenically unsaturated monomer (Ib), and
ic) between 0% and 15%, such as between 0% and 5% by weight over the weight of the combination of a ionized or ionizable monoethylenically unsaturated monomer (Ic).

Adopting the above combination of monomers (Ia) to (Ic) allows to obtain microcapsules which display shell properties which are pH-independent in a pH range commonly met in liquid household, laundry personal care and cosmetic products, such as fabric conditioners and antiperspirants (acidic pH) or liquid laundry detergents and hard surface cleaners (alkaline pH). For example, this pH range is comprised between 2 and 12, such as more than 4, for example between 4 and 12. Hence, it is particularly advantageous that a product (as defined below) including a microcapsule obtainable with that blend is liquid at room temperature and has a pH of, for example, more than 4, such as more than 4 and less than 12.

In the present description and unless otherwise indicated, "neutral" means that the monomethacrylate monomer is non-ionized or ionized in an amount of less than 20 mol % when measured in deionized water at 20° C. at a pH of 2 and 12. For example, a monomethacrylate monomer is neutral if it does not contain functional groups which are permanently ionized such as quaternized amines, for example quaternary alkyl ammonium salts. For example, a neutral monomethacrylate monomer may contain functional groups whose protonated species have $pK_a$ greater than about 12.5, such as greater than about 12.7, for example greater than about 13, such as comprised between about 13 and 30. For example, a monomethacrylate monomer is neutral if it does not contain functional groups such as carboxylic acid groups, primary or secondary amine groups. Alternatively, a neutral monomethacrylate monomer may contain functional groups such as primary alcohols, primary or secondary amides or ether groups.

Monomer (Ia) has a solubility in water at pH 7 and 20° C. equal to, or more than 2 g/100 ml, for example more than 3 g/100 ml, such as more than 4 g/100 ml or more than 5 g/100 ml. Monomer (Ia) is a hydrophilic one. Water solubility is conveniently measured according to OECD method 105—water solubility adopted on 27 Jul. 1995 (OECD GUIDELINE FOR THE TESTING OF CHEMICALS).

Monomer (Ia) may be selected from 2-hydroxyethyl methacrylate, 2-hydroxypropyl methacrylate, 3-hydroxypropyl methacrylate, methacrylamide, glycidyl methacrylate, methacrylonitrile, poly(ethylene glycol) methyl ether methacrylate, for example PEG300 methacrylate methyl ether or for example a poly(ethylene glycol) methyl ether methacrylate wherein the average number of PEG units is comprised between 3 and 20, for example between 5 and 10 (e.g. triethylene glycol methyl ether methacrylate; tetraethyleneglycol methyl ether methacrylate; penta ethyleneglycol methyl ether methacrylate; decaethyleneglycol methyl ether methacrylate; pentadecaethyleneglycol methyl ether methacrylate), and mixtures thereof. For example, monomer (Ia) may be selected from 2-hydroxyethyl methacrylate, 2-hydroxypropyl methacrylate, 3-hydroxypropyl methacrylate, glycidyl methacrylate, triethylene glycol methyl ether methacrylate; PEG300 methacrylate methyl ether, and mixtures thereof. For example, monomer (Ia) may be selected from 2-hydroxyethyl methacrylate, glycidyl methacrylate, poly (ethylene glycol) methyl ether methacrylate and mixtures thereof.

Preferably, monomer (Ia) includes at least 2-hydroxyethyl methacrylate. For example, 2-hydroxyethyl methacrylate may represent at least 10% or at least 20% or at least 30% or at least 40% or at least 50% or at least 60% or at least 70% or at least 80% or at least 90% by weight of the monomer (Ia) in the blend. Monomer (Ia) may consist of 2-hydroxyethyl methacrylate.

Monomer (Ib) is a neutral monoethylenically unsaturated monomer other than, i.e. different from monomer (Ia). Neutral is defined as discussed above.

Suitable examples of monomers (Ib) may be:
optionally substituted $C_1$-$C_{24}$ linear or branched alkyl esters of $C_3$-$C_6$ monoethylenically unsaturated mono- or poly carboxylic acids, and
optionally substituted $C_3$-$C_6$ cycloalkyl esters of $C_3$-$C_6$ monoethylenically unsaturated mono- or poly carboxylic acids.

Optional substituents may be —OH, —OR, —C(O)R, wherein R is $C_1$-$C_4$ alkyl while a preferred mono- or poly carboxylic acid is methacrylic acid.

Monomer (Ib) may conveniently have a solubility in water at pH 7 and 20° C. of less than 2 g/100 ml. It may be totally insoluble in water. Monomer (Ib) is a hydrophobic one. Water solubility is conveniently measured according to OECD method 105—water solubility adopted on 27 Jul. 1995 (OECD GUIDELINE FOR THE TESTING OF CHEMICALS).

Monomer (Ib) may be selected from methyl methacrylate, ethyl methacrylate, n-propyl methacrylate, isopropyl methacrylate, tert-butyl methacrylate, isobutyl methacrylate, n-butyl methacrylate, benzyl methacrylate, isobornyl methacrylate, cyclohexyl methacrylate, tetrahydrofurfuryl methacrylate, mono(ethylene glycol) methyl ether methacrylate, di(ethylene glycol) methyl ether methacrylate, and mixtures thereof. For example, monomer (Ib) may be selected from methyl methacrylate and/or ethyl methacrylate.

Preferably, monomer (Ib) includes at least methyl methacrylate. Preferably, monomer (Ib) includes at least ethyl methacrylate. For example, methyl methacrylate and/or ethyl methacrylate may be present in an amount of at least 10%, such as at least 20%, for example at least 30%, such as at least 40%, or at least 50%, or at least 60%, or at least 70%, such as at least 80%, for example at least 90% by weight over the combined weight of all monomers (Ib) present in the blend. Monomer (Ib) may consist of methyl methacrylate and/or ethyl methacrylate.

Monomer (Ic) is a ionized or ionizable monoethylenically unsaturated monomer.

In the present description and unless otherwise indicated, "ionized or ionizable" means that monomer (Ic) is either permanently ionized or ionized in an amount of more than 20 mol % when measured in deionized water at 20° C. at a pH of either 2 or 12. For example, monomer (Ic) is ionized or ionizable if it contains functional groups which are permanently ionized such as quaternized amines, for example quaternary alkyl ammonium salts. For example, monomer (Ic) may contain functional groups whose protonated species have $pK_a$ lower than about 12.5, such as lower than about 11, for example lower than about 10, such as comprised between about 10 and 0. For example, a ionized or ionizable monomer (Ic) may contain one or more of functional groups such as carboxylic acid groups, sulfonic acid groups and primary or secondary amine groups.

Examples of monomer (Ic) are (meth)acrylic acid, 3-(methacryloylamino)propyl]trimethylammonium chloride, dimethyldiallyl ammonium chloride, maleic acid, itaconic acid, 2-(diethylamino)ethyl methacrylate, dimethylaminoethyl methacrylate, 2-(tert-Butylamino)ethyl methacrylate, N-[3-(dimethylamino)propyl]methacrylamide, acryloxyethyltrimethyl ammonium chloride, 2-ethyl(2-oxoimidazolidin-1-yl)methacrylate and mixtures thereof. Preferred examples are methacrylic acid and/or 3-(methacryloylamino)propyl]trimethylammonium chloride.

Compound (II) is a polyethylenically unsaturated monomer. Compound (II) may also be referred to as crosslinker due its crosslinking function in the manufacturing of the capsule shell.

Compound (II) may be a di- or poly(meth)acrylate monomer meaning that it contains two or more (meth)acrylate ester or amide groups.

Examples of $C_2$-$C_{24}$ alkyl di- or polyamide of (meth)acrylic acid are N,N-methylenebis(2-methyl(meth)acrylamide), N,N-ethylenebis(2-methyl(meth)acrylamide) and the amides obtainable by reacting melamine with (meth)acrylic acid.

Preferably, compound (II) is selected from the group consisting of a $C_2$-$C_{24}$ alkyl di- or polyester of methacrylic acid, a $C_2$-$C_{24}$ alkyl di- or polyamide of methacrylic acid and mixtures thereof, such as a $C_2$-$C_{24}$ alkyl di- or polyester of methacrylic acid, a $C_2$-$C_{24}$ alkyl di- or polyamide of methacrylic acid and mixtures thereof, for example a $C_2$-$C_{24}$ alkyl di- or polyester of methacrylic acid.

Suitable di- or polyesters are those resulting from the esterification of methacrylic acid with linear or branched polyhydric $C_2$-$C_{24}$, such as $C_2$-$C_{12}$, alcohols or $C_2$-$C_{24}$, such as $C_2$-$C_{12}$, polyethylene glycols. Suitable polyhydric alcohols may be those having a number average molecular weight of up to about 6000. Suitable polyethylene glycols may be those having a number average molecular weight of up to about 7500. Polyhydric alcohols are advantageously diols. Polyethylene glycols are advantageously di-, tri- or tetra-ethylene glycols.

Examples of compound (II) are 1,4-butylene glycol dimethacrylate (molecular weight MW about 226); 1,3-butylene glycol dimethacrylate (MW about 226); pentaerythritol trimethacrylate (MW about 340); glycerol trimethacrylate (MW about 296); 1,2-propylene glycol dimethacrylate (MW about 212), 1,3-propylene glycol dimethacrylate (MW about 212), ethylene glycol dimethacrylate (MW about 198), diethylene glycol dimethacrylate (MW about 242); glycerol dimethacrylate (MW about 228); 1,6-hexane diol dimethacrylate (MW about 226), trimethylolpropane trimethacrylate (MW about 338); ethoxylated pentaerythritol tetramethacrylate (MW about 585), and mixtures thereof. Preferred examples are 1,4-butylene glycol dimethacrylate, 1,3-propylene glycol dimethacrylate, ethylene glycol dimethacrylate, diethylene glycol dimethacrylate and mixtures thereof, such as 1,4-butylene glycol dimethacrylate, ethylene glycol dimethacrylate, 1,3-propylene glycol dimethacrylate and mixtures thereof.

Compound (II) may include at least 1,4-butylene glycol dimethacrylate, 1,3-propylene glycol dimethacrylate, ethylene glycol dimethacrylate or diethylene glycol dimethacrylate, such as at least 1,4-butylene glycol dimethacrylate and/or ethylene glycol dimethacrylate and/or 1,3-propylene glycol dimethacrylate. For example, compound (II) may include at least, or consist of, 1,4-butylene glycol dimethacrylate. For example, compound (II) may include at least, or consist of, ethylene glycol dimethacrylate. For example, compound (II) may include at least, or consist of, 1,3-propylene glycol dimethacrylate. For example, compound (II) may include the above crosslinkers in an amount of at least 10%, such as at least 20%, for example at least 30%, such as at least 40%, or at least 50%, or at least 60%, or at least 70%, such as at least 80%, for example at least 90% by weight over the combined weight of compound (II) in the blend.

In one aspect, compound (II) is a $C_2$-$C_{24}$ alkyl di- or polyester of (meth)acrylic acid, preferably methacrylic acid, and:

A1. It contains two or more, for example 2 to 6, or 2 to 4 such as 2 or 3 or 4 (meth)acrylate ester or amide groups per monomer, and B1. It has a MW (molecular weight, expressed as mass units) which, once divided by the number of (meth)acrylate ester or amide groups, gives a value of more than about 85, for example more than about 90, and lower than about 135, such as lower than about 121.

In one embodiment, compound (II) meets conditions A1 and B1 above provided that any one or more of 1,4-butylene glycol dimethacrylate, ethylene glycol dimethacrylate, 1,3-propylene glycol dimethacrylate, ethylene glycol dimethacrylate and diethylene glycol dimethacrylate are excluded.

In one aspect, compound (II) may be a polyethylenically unsaturated monomer as defined above such that the microcapsule provides for a fragrance leakage of less than about 35%, such as less than about 28%, for example less than about 22%, when tested upon storage for 4 weeks at 40° C. in a test liquid base, according to a leakage test method, when the microcapsule is prepared according to a general manufacturing procedure, and the microcapsule encapsulates fragrance no. 5, the test liquid base, the leakage test method, the general manufacturing procedure and the fragrance no. 5 being as defined in the examples presently enclosed.

In one embodiment, compound (II) meet the above leakage condition provided that any one or more of 1,4-butylene glycol dimethacrylate, ethylene glycol dimethacrylate, 1,3-propylene glycol dimethacrylate, ethylene glycol dimethacrylate and diethylene glycol dimethacrylate are excluded.

Compound (II) may be present between 30 and 60%, or between 35 and 60%, or between 40 and 55% by weight over the combined weight of compounds (I) to (III).

Compound (III) may be a monomethacrylate silane monomer and/or a silane chain transfer agent.

A suitable monomethacrylate silane monomer may have formula (X):

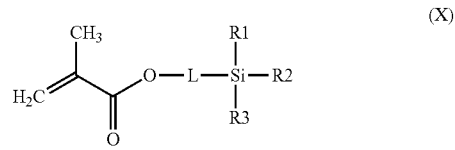

wherein:

R1, R2 and R3 are each independently selected from the group consisting of methoxy, ethoxy, and methyl, provided that at least two of R1, R2 and R3 are methoxy or ethoxy; L is an spacer group, for example a $C_1$-$C_4$ alkyl spacer group, such as a $C_1$-$C_4$ linear alkyl spacer group, which may include a carbamate (i.e. —OC(O)NH—) group. Examples of L spacer groups may be —$(CH_2)_2$—, —$(CH_2)_3$— and —$(CH_2)_2$—O—C(O)—NH—$(CH_2)_2$—. For example, —$(CH_2)_3$— spacer group is preferred.

A suitable silane chain transfer agent is mercaptopropyltrimethoxysilane.

Commercially available examples of compound (III) are:
i. methacryloxypropyltrimethoxysilane CAS No. 2530-85-0;
ii. methacryloxypropyltriethoxysilane CAS No. 21142-29-0;
iii. mercaptopropyltrimethoxysilane CAS No. 4420-74-0;
iv. o-(methacryloxyethyl)-N-(triethoxysilylpropyl)urethane CAS No. 115396-93-5;
v. methacryloxymethyltrimethoxysilane CAS No. 54586-78-6;
vi. (methacryloxymethyl)methyl diethoxysilane CAS No. 121177-93-3;

vii. (methacryloxymethyl)methyl dimethoxysilane CAS No. 3978-58-3;
and
viii. mixtures thereof.

For example, compound (III) may include at least, such as consist of, methacryloxypropyltrimethoxysilane and/or methacryloxypropyltriethoxysilane. For example, monomer (III) may include at least, such as consist of, methacryloxypropyltrimethoxysilane. For example, monomer (III) may include at least, such as consist of, methacryloxypropyltriethoxysilane.

Monomer (III) may be present between 0.5 and 10%, such as between 0.5 and 5%, or between 1 and 5% by weight over the combined weight of compounds (I) to (III).

The blend may include, such as consist of:
between 20 and 60%, such as between 35 and 60% of compound (I),
between 20 and 70%, such as between 35 and 60% of compound (II) and
between 0.5 and 10%, such as between 0.5 and 5% of compound (III),
over the combined weight of compounds (I) to (III).

For example, the shell comprises in polymerized form a blend including, such as consisting of:
i) between 20% and 60%, preferably between 30% and 60% by weight over the combined weight of compounds (I) to (III) in the blend of a compound (I) which is a combination of methacrylic acid with methyl or ethyl methacrylate;
ii) between 20% and 70%, preferably between 30% and 60% by weight over the combined weight of compounds (I) to (III) in the blend of a compound (II) which is selected from a $C_2$-$C_{24}$ alkyl di- or polyester of methacrylic acid, a $C_2$-$C_{24}$ alkyl di- or polyamide of methacrylic acid and mixtures thereof, such as a monomer selected from 1,4-butane diol dimethacrylate, ethylene glycol dimethacrylate, 1,3-propylene glycol dimethacrylate and mixtures thereof, and
iii) between 0.5% and 10%, preferably between 0.5% and 5% by weight over the combined weight of compounds (I) to (III) in the blend of a compound (III) which is methacryloxypropyltrimethoxysilane and/or methacryloxypropyltriethoxysilane.

For example, the shell comprises in polymerized form a blend including, preferably consisting of:
i) between 20% and 70%, such as between 30% and 60% by weight over the combined weight of compounds (I) to (III) in the blend of a compound (I) which is a combination of:
   ia) between 70% and 100% by weight over the weight of the combination of 2-hydroxyethyl methacrylate;
   ib) between 0% and 30% by weight over the weight of the combination of a $C_1$-$C_{24}$ linear or branched alkyl ester of methacrylic acid such as methyl and/or ethyl methacrylate;
   ic) between 0% and 5% by weight over the weight of the combination of methacrylic acid and/or 3-(methacryloylamino)propyl]trimethylammonium chloride;
ii) between 20% and 70%, such as between 30% and 60% by weight over the combined weight of compounds (I) to (III) in the blend of a compound (II) which is selected from a $C_2$-$C_{24}$ alkyl di- or polyester of methacrylic acid, a $C_2$-$C_{24}$ alkyl di- or polyamide of methacrylic acid and mixtures thereof, such as a monomer selected from 1,4-butane diol dimethacrylate, ethylene glycol dimethacrylate, 1,3-propylene glycol dimethacrylate and mixtures thereof, and
iii) between 0.5% and 10%, such as between 0.5% and 5% by weight over the combined weight of compounds (I) to (III) in the blend of a compound (III) which is methacryloxypropyltrimethoxysilane and/or methacryloxypropyltriethoxysilane.

The blend may consist of compounds (I) to (III) as presently defined, meaning that the combined amounts of compounds (I) to (III) make 100% of the weight of the blend.

The blend may be substantially free of monoethylenically unsaturated monomers other than compounds (I) and (III) as presently defined.

The blend may be substantially free of polyethylenically unsaturated monomers other than compound (II) as presently defined.

The blend may be substantially free of one or more of:
monomers, such as acrylic acid, which contain carboxylic acid (—COOH) groups and/or primary or secondary amine groups, in either neutral or ionized form;
$C_1$-$C_{24}$ alkyl monoesters of acrylic acid;
$C_2$-$C_{24}$ alkyl poly (e.g. di-, tri-, tetra- or penta) esters of acrylic acid (crosslinkers);
monomers containing a carboxyl anhydride group (e.g. a monomer containing symmetric or asymmetric intermolecular anhydrides of monoethylenically unsaturated monocarboxylic acids having 3 to 20 carbon atoms);
monomers containing alkylenebis(meth)acrylamide group (e.g. N,N'-unsubstituted $C_{1-18}$ alkylene bis(meth)acrylamides or linear or cyclic N,N'-substituted $C_{1-18}$ alkylene bis(meth)acrylamides wherein substituents are selected from $C_{1-8}$ alkyl, $C_{1-8}$ hydroxyalkyl or polyoxy($C_{1-4}$)alkylene of 2 to 500 alkylene units or the alkyl substituents together with the nitrogen atoms to which they are attached form a 5- to 8-membered ring).

The blend is preferably substantially free of $C_1$-$C_{24}$ alkyl monoesters of acrylic acid and/or $C_2$-$C_{24}$ alkyl polyesters of acrylic acid. For example, it is preferred that the blend be substantially free of acrylic acid, $C_1$-$C_{24}$ alkyl monoesters of acrylic acid, $C_2$-$C_{24}$ alkyl polyesters of acrylic acid and $C_2$-$C_{24}$ alkyl polyamides of (meth)acrylic acid. For example, the blend may be substantially free of acrylic and/or methacrylic acid, $C_1$-$C_{24}$ alkyl monoesters of acrylic acid, $C_2$-$C_{24}$ alkyl polyesters of acrylic acid and $C_2$-$C_{24}$ alkyl polyamides of (meth)acrylic acid.

In the present disclosure, and unless otherwise indicated, substantially free mean less than 5% such as less than 1%, for example 0% by weight over the weight of the blend.

The perfume composition includes a fragrance, i.e. an olfactively active (i.e. odoriferous) material typically but not necessarily providing a pleasant smell.

The perfume composition may represent at least 50%, such as at least 60% by weight of the weight of dried slurry. The perfume composition may represent up to 90%, such as up to 80% by weight of the weight of dried slurry. Unless otherwise indicated, dried slurry means the product obtainable by subjecting a microcapsule slurry as defined below to the solid content measurement method as discussed in the examples.

The perfume composition presently disclosed may include, such as consist of, a fragrance, or it may also include a perfumery acceptable solvent and/or a benefit agent. For example, the fragrance may represent at least 40%, such as at least 60%, for example at least 80%, such as at least 90% by weight over the weight of the perfume composition. The balance of the perfume composition may be represented by perfumery acceptable solvents and/or benefit agents as defined below.

The fragrance may consist of a single, typically organic, molecule or a mixture of distinct molecules. Hereinafter, these molecules will also be referred to as "perfumery molecules". Fragrance typically used in the field of perfumery and suitable for the purposes of the present disclosure are described more fully in S. Arctander, Perfume Flavors and Chemicals 1969, Vols. I and II, Montclair, N.J and in Allured's Flavor and Fragrance Materials 2007 ISBN 978-1-93263326-9 published by Allured Publishing Corp. The term fragrance comprises both naturally occurring as well as synthetic fragrances known for use in perfumes. Perfumery molecules advantageously display balanced volatility/hydrophobicity so as to be olfactively noticeable when the microcapsules release them but also sufficiently water-insoluble to be emulsified during encapsulation.

The perfume composition may comprise at least two, such as at least four, or at least eight distinct fragrances.

For example a fragrance may comprise at least two distinct perfumery molecules whose combination does not display a solid-liquid phase transition at a temperature comprised between −20° C. and 120° C.

A fragrance may comprise one or more distinct perfumery molecules each having a molecular weight greater than 100, preferably greater than 125 and lower than 325, preferably lower than 300, more preferably lower than 275. A fragrance may comprise one or more distinct perfumery molecules each having a boiling point comprised between about 80° C. and 400° C., such as between about 100° C. and 350° C. when measured at 760 mm Hg. It is preferable that perfumery molecules have water solubility below 1.5 g/100 ml at 20° C. It is possible for example that a fragrance according to the present disclosure contains at least 80% by weight over the weight of the fragrance of a perfumery molecule as defined above. For example, at least 90% by weight over the weight of all perfumery molecules present in the fragrance may be represented by one or more perfumery molecules having water solubility at 20° C. comprised between 0.0005 g/100 ml, such as 0.002 g/100 ml, and 1 g/100 ml.

In conditions that may be encountered during conventional suspension free radical polymerization, certain commonly used fragrances have experimentally been found to favor an unsatisfactory formation of latex particles and/or an imperfect capsule shell formation. The combined use of solid colloidal particles and a silane compound as presently defined has been found to reduce both unwanted effects thereby permitting a satisfactory encapsulation of many commonly used fragrances. This also results in achieving the formation of a still satisfactory (e.g. endowed with an improved physical resistance) microcapsule shell and ultimately reducing the leakage of the final microcapsule.

For example, advantages have been found when the fragrance (or the mixture of fragrances) included in the perfume composition is such that a microcapsule comprising said perfume composition has a span ratio of greater than about 1.3, for example greater than about 1.3 and less than 5 when obtained according to the fragrance test manufacturing procedure, the span ratio and the manufacturing procedure being in the present examples.

The above protocol (wherein no compound (III) as presently defined is used) can be easily followed and the result directly and positively verified.

With references to the examples presently enclosed, microcapsules showing a span ratio falling within the above range may be obtained when encapsulating fragrances which include one or more the following perfumery molecules: cyclacet (CAS No 54830-99-8), Iso E super (CAS No 54464-57-2 166090-45-5), allyl heptoate (CAS No 142-19-8), delta damascone (CAS No 57378-68-4), linalool (CAS No 78-70-6), linalyl acetate (CAS: 115-95-7), pinene beta (CAS No 127-91-3), citral (CAS No 5392-40-5), dihydromyrcenol (CAS: 18479-58-8), geraniol (CAS: 106-24-1), patchouli oil de-ironized natural (supplier: Reynaud™, CAS: 84238-39-1), (E,Z)-2,6-nonadien-1-ol (CAS: 28069-72-9), damascenone (CAS: 23726-93-4), isofreshal (CAS: 68259-31-4), vanitrope (CAS: 94-86-0), benzyl salicylate (CAS: 118-58-1), triplal (CAS: 27939-60-2), allyl caproate (CAS: 123-68-2), isocyclocitral (CAS: 1335-66-6), galbascone BHT (CAS: 56973-85-4, 128-37-0) (Supplier: IFF), ambretone (CAS: 37609-25-9) and karanal (CAS: 117933-89-8).

It is convenient that fragrances for incorporation in a perfume composition as presently disclosed be selected so that the perfume composition contains less than 25%, such as less than 15%, for example less than 5% by weight of a perfumery molecule selected from the group consisting of limonene (CAS: 5989-27-5), carvone (CAS: 99-49-0, 2244-16-8), ethyl safranate (CAS: 35044-57-6), myrcene (CAS: 123-35-3), myrcenol (CAS: 543-39-5), myrcenyl acetate (CAS: 1118-39-4), eugenol (CAS: 97-53-0), eugenyl acetate (CAS: 93-28-7), chavicol (CAs: 501-92-8), estragol (CAS: 140-67-0), anethol (CAS: 104-46-1), and mixtures thereof.

The perfume composition may also include a perfumery acceptable solvent. Solvents are conventionally used in the fragrance industry to dilute olfactively powerful ingredients and to facilitate the handling of solid ingredients by dissolving them and handling them as liquids, or simply as a diluent to reduce overall fragrance cost per unit weight. Typically, suitable solvents are water-immiscible solvents, for example solvents having water solubility of less than 10 g/L. Examples of perfumery acceptable solvents are water insoluble hydrocarbon solvents (such as the Isopar® family from ExxonMobil), benzyl benzoate, isopropyl myristate, dialkyl adipates, citrate esters (such as acetyl triethyl citrate and acetyl tributyl citrate) and diethyl phthalate. If present, water miscible solvents (e.g. solvents with water solubility of more than 10 g/100 ml), such as propylene glycol dipropylene glycol, and butylene glycols should preferably be dosed at as low level as possible.

The perfume composition may also include benefit agents. Benefit agents are typically emulsifiable materials having synthetic or natural origin and which can survive storage to deliver a benefit through the use a product containing the microcapsules, such as household, personal care or cosmetic products. Examples of benefit agents are:
  agents which suppress or reduce malodour and its perception by adsorbing odour such as zinc ricinoleate,
  agents improving microcapsule physical-chemical properties such as sucrose octa-acetate or sucrose hexabutyrate di-acetate,
  gelling agents such as hydroxy fatty acids or the Sylvaclear™ range of materials available from Arizona Chemicals,
  agents which provide a warming or cooling effect such as cyclohexane carboxamide N-ethyl-5-methyl-2-(1-methylethyl); N 2,3-trimethyl-2-isopropylbutamide; menthyl lactate; (−)-menthoxypropane 1,2-diol,
  insect repellents such as ethylbutylacetylaminopropionate; N,N-diethyl toluamide; 1-piperidinecarboxylic acid; 2-(2-hydroxyethyl)-1-methylpropyl ester; p-menthane-3,8-diol, antimicrobial agents such as Triclosan™ compound having CAS No 3380-34-5, or the methyl, ethyl, propyl and butyl para hydroxy benzoate esters, UV absorbers such as octyl methoxycinnamate, butylmethoxydibenzoylmethane, and bis ethylhexyloxyphenolmethoxyphenyltriazine.

Microcapsules may be prepared using a range of known conventional methods such as coacervation, interfacial polymerization, free radical polymerization, or polycondensation. These techniques are well-know, see e.g., U.S. Pat. No. 3,516,941, U.S. Pat. No. 4,520,142, U.S. Pat. No. 4,528,226, U.S. Pat. No. 4,681,806, U.S. Pat. No. 4,145,184; GB-A-2073132; WO99/17871; and MICROENCAPSULATION Methods and Industrial Applications Edited by Benita and Simon (Marcel Dekker, Inc. 1996).

Advantageously, the microcapsules presently disclosed are manufactured by suspension free radical polymerization (i.e. a free radical polymerization wherein polymerization is triggered within the oil phase). Accordingly, the present disclosure discloses a suspension free radical polymerization process for the manufacture of the microcapsule as defined above, which includes the following steps:

a) providing an oil-in-water emulsion having an oil phase and a water phase, said emulsion being obtainable by mixing:
  colloidal silica particles having an average primary particle size comprised between 5 nm and 1 μm,
  an oil soluble polymerization initiator,
  a perfume composition including a fragrance,
  the blend as defined above, and
  a protective colloid,
b) triggering polymerization within the oil phase of the emulsion obtained in step a),
c) letting the polymerization propagate thereby obtaining microcapsules.

Steps a) to c) may be performed in the order in which they are presented. Steps a) and b) can be performed according to a separate or sequential time order. In effect, since the emulsion presently disclosed is a Pickering one, it is endowed with sufficient stability so as to be obtained (in step a)) and then either sequentially proceeded to step b) or stored. In the latter case, step b) can be performed in the same or different location (e.g. reactor) where step a) was performed and/or at a separate time with respect to step a). Accordingly, the emulsion which is obtainable at the end of step a) may, if so desired, be isolated and/or physically transferred.

Although there is no intention to be bound by any theory, it is believed that the advantageous effects presently disclosed in relation to interfacial polymerization, latex formation, capsule shell physical resistance and capsule leakage stem from a chemical interaction between the silane compound and the solid colloidal particles which leads to the creation of a new physical entity positioned at phase interface of the oil-in-water emulsion.

The microcapsules are conveniently prepared through a polymerization step. The polymerization may be conventional radical polymerization or living radical polymerization. Such radical polymerization processes are known to persons skilled in the art and are further described e.g. in Moad, Graeme; Solomon, David H.; The Chemistry of Radical Polymerization, $2^{nd}$ ed.; Elsevier, 2006.

A discussion of living radical polymerization, can be found for example in Braunecker, Wade A.; Matyjaszewski, Krzysztof; "Controlled/Living Radical Polymerization: Features, Developments, and Perspectives"; Progress in Polymer Science 2007, Volume 32, Issue 1, Pages 93-146.

The monomers of the blend are as defined above. They are weighed and mixed so as to obtain a monomer blend as defined above. Then, this blend is used in the preparation of the oil-in-water emulsion.

An oil-in-water emulsion (step a) of the process) may be prepared by mixing and dissolving the oil soluble ingredients into a homogeneous solution while separately mixing and dissolving the water soluble ingredients into a homogenous solution. Solid colloidal particles are typically admixed to the water solution. An emulsion may be obtained by mixing e.g. with a high shear mixer and for sufficient time the two solutions to create a stable emulsion of a desired particle size. At the same time the emulsion may be purged with nitrogen or other inert gas. Once the air has been removed, polymerization may be heat induced (step b)) by elevating the temperature. The exact temperature and rate of temperature increase is determined by the initiator or combination of initiators to be used. Typically polymerization temperatures are between 40° C. to 90° C. The rate of polymerization can be controlled in a known manner by appropriate choice of the temperature and amount of polymerization initiator for the particular monomers and initiator in an experiment. Once the polymerization temperature has been reached, polymerization continues (step c)) for a further period, for example 2 to 6 hours, in order to complete the reaction of the monomers.

For example, the oil homogenous solution may include the initiator, the perfume composition and the (monomeric) blend while the water homogenous solution may include the particulate colloid. An emulsifier (e.g. a protective colloid) may be added after creating a stable emulsion to further stabilize the oil-in-water emulsion before triggering polymerization.

Water-soluble initiators can be added later in the polymerization to reduce the level of residual compounds (I) to (III). Further compounds (I) to (III) may be added during the course of the reaction to control dosage. Salts may be added e.g. to buffer the pH.

The emulsion includes an oil-soluble polymerization initiator, hence suitable to perform suspension polymerization. A water soluble initiator may optionally be added as disclosed above. Radicals can be generated by thermal decomposition of compounds such as peroxy and azo compounds, or by photolysis with UV radiation or by redox reactions. Examples of oil-soluble initiators are:
  oil-soluble thermal polymerization initiator, and/or
  oil-soluble photopolymerization initiator, and/or
  oil-soluble redox initiator including a radical-generating reductant/oxidant pair.

Oil-soluble thermal polymerization initiators may be present in an amount comprised between 0.1% and 5% by weight over the combined weight of compounds (I) to (III) in the blend. Examples of oil-soluble thermal polymerization initiator are:
  dilauroyl peroxide,
  benzoyl peroxide,
  α,α'-azoisobutyronitrile,
  2,2'-azobis(2.4-dimethyl valeronitrile),
  dimethyl 2,2'-azobis(2-methylpropionate),
  1,1'-azo-bis-1-Cyclohexanenitrile,
  di-tert-butyl peroxide (CAS: 75-91-2),
  2,2'-azobis[2-(2-imidazolin-2-yl)propane],
  2,2'-azobis[2-methyl-N-(2-hydroxyethyl)propionamide], and
  mixtures thereof.

Oil-soluble photopolymerization initiators may be present in an amount comprised between 0.5% and 5% by weight over the combined weight of compounds (I) to (III). Examples of oil-soluble photopolymerization initiator are:
- alpha hydroxyl ketones,
- alpha amino ketones,
- alpha and beta naphthyl carbonyl compounds,
- benzoin ethers such as benzoin methyl ethers,
- benzophenone,
- acetophenone,
- benzaldehyde,
- xanthone,
- 9,10-anthraquinone,
- 1-hydroxy-cyclohexyl-phenyl-ketone (Irgacure™ 184), and
- mixtures thereof.

Suitable examples of water-soluble initiators that can be used as disclosed above are: 2,2'-Azobis[2-(2-imidazolin-2-yl)propane]dihydrochloride (CAS: 27776-21-2), 2,2'-Azobis(2-methylpropionamidine)dihydrochloride (CAS: 2997-92-4), 2,2'-Azobis[N-(2-carboxyethyl)-2-methylpropionamidine]hydrate (CAS: 291314-39-1), salts of peroxodisulfuric acid such as sodium persulfate (CAS: 7775-27-1), potassium persulfate (CAS: 7727-21-1), ammonium persulfate (CAS: 7727-54-0), redox initiators wherein in the radical-generating reductant/oxidant pair:
- the oxidant may be selected from salts of peroxodisulfuric acid such as sodium persulfate, potassium persulphate, ammonium persulfate, cumene hydroperoxide (CAS: 80-15-9), tert-butyl hydroperoxide (CAS: 75-91-2), and hydrogen peroxide (CAS: 7722-84-1), and
- the reductant may be selected from sodium sulphite (CAS: 7757-83-7), sodium metabisulphite (CAS: 7681-57-4), ascorbic acid (CAS: 50-81-7), sodium dithionite (CAS: 7775-14-6), and ferrous and copper salts.

Protective colloids and/or surfactants are conventionally used in emulsion polymerization and in suspension polymerization to stabilize oil-in-water emulsions created by mechanical agitation while the polymerization occurs.

A suitable protective colloid has an average molecular weight comprised between 500 and 1,000,000 g/mol, for example between 1,000 and 500,000 g/mol.

Suitable water miscible polymeric protective colloids are:
- cellulose derivatives such as hydroxyethylcellulose, carboxymethylcellulose and methylcellulose,
- polyvinylpyrrolidone,
- copolymers of N-vinylpyrrolidone,
- polyvinyl alcohols obtainable by full to partial hydrolyses of polyvinyl acetates,
- polyacrylic and/or polymethacrylic acid,
- copolymers of acrylic acid and methacrylic acid,
- ionic colloids such as sulphonic-acid-group-containing water-soluble polymers (e.g. 2-acrylamido-2-alkylsulphonic acids and styrene sulphonic acids), and
- mixtures thereof.

Advantageously, the protective colloid is a water-soluble protective colloid. Preferably, this means that the colloid has solubility in water of at least 5 g/L at 20° C.

Advantageously, the protective colloid includes at least polyvinyl alcohol (PVA), such as a PVA obtainable by full to partial hydrolyses of polyvinyl acetates.

The protective colloid may be present in an amount comprised between 0.1% and 10% by weight over the weight of the water phase of the oil-in-water emulsion.

Step b) entails inducing decomposition of polymerization initiator. Polymerization is initiated in the oil phase of the emulsion. Step b) may comprise:
- subjecting the oil-in-water emulsion to heat, and/or
- subjecting the oil-in-water emulsion to UV light.

The microcapsules of the invention may also comprise on their surface (e.g. surface grafted) deposition aids, i.e. aids aiming to optimize the deposition of microcapsule on the intended substrate (examples of substrates are hair, skin and fabrics such as cotton).

Examples and use of deposition aids on microcapsules are for example disclosed in EP21558474, EP1572767, EP2188364 and EP1019478.

The deposition aid may be present in an amount comprised between 0.1% and 10% by weight over the dry weight of a microcapsule.

The deposition aid may be a polymeric deposition aid. Examples may be synthetic or natural polymers or combinations thereof (e.g. through partial chemical modification of natural polymers).

The deposition aid may be a peptide, a protein, or a chemical derivative thereof, providing for a binding to the intended substrates. For example cellulases bind to cotton while proteases bind to wool, silk or hair.

The deposition aid may be a polysaccharide or a chemical derivative thereof. The polysaccharide preferably has a [beta]-1,4-linked backbone. Examples of polysaccharide are cellulose, a cellulose derivative, or another [beta]-1,4-linked polysaccharide binding to cellulose, such as polymannan, polyglucan, polyglucomannan, polyxyloglucan and polygalactomannan or mixtures thereof. For example, the polysaccharide is selected from the group consisting of polyxyloglucan and polygalactomannan. Highly preferred polysaccharides are selected from locust bean gum, tamarind gum, xyloglucan, non-ionic guar gum, cationic starch and mixtures thereof. For example, the deposition aid is locust bean gum, or chemical derivatives thereof.

In one embodiment, the process presently disclosed may include a step d) to be performed after step c) and including binding a deposition aid to the microcapsules. The deposition aid may be adsorbed to the microcapsule shell or physically and/or chemically bonded to the microcapsule shell. Adsorption (i.e. physical binding) of the deposition aid to the already-formed microcapsule shell may rely on hydrogen bonding, Van Der Waals or electrostatic attraction between the deposition aid and the microcapsule. The deposition aid is thus external to the microparticle and is not, to any significant extent, within the shell and/or within the microcapsule core.

Alternatively, a deposition aid may be part of the emulsion provided in step a). In this case, the deposition aid will be integral part of the microcapsule shell. This situation is known as "entanglement". By entanglement as used herein is meant that the deposition aid is partially buried within the interior of the microcapsule. This is obtained by adding the deposition aid to the emulsion e.g. before the polymerization is triggered. By letting the polymerization propagate, part of the deposition aid remains entrapped and bound in the extending polymer that will form the microcapsule shell whilst the remainder is free to extend into the aqueous phase of the emulsion. In this manner, the deposition aid is only partially exposed at the microcapsule surface.

In one aspect, the present disclosure discloses a water-based dispersion comprising a microcapsule as defined above, for example a plurality of microcapsules as defined above (also referred to as "slurry" or "slurry dispersion").

The water-based dispersion may be obtainable by a suspension free radical polymerization process as disclosed above.

The water-based dispersion is substantially free of latex particles. In this context "substantially free" is understood as meaning that the dispersion can contain up to 5% by volume of latex particles based on the total volume of the dispersed phase (dispersed phase=microcapsules+latex particles).

The dispersion may conveniently be used to prepare e.g. liquid products that will be discussed later in this disclosure. The slurry functions thus as a concentrated fluid which is added to the liquid products. Since this process entails a substantial dilution of the slurry components, microcapsules are contained in the slurry in amounts that are higher than the target amount in the final products. For this reasons, the dispersion may contain microcapsules in amounts of at least 30%, such as at least 40%, or at least 50%, or at least 60%, by weight over the weight of the dispersion (wherein percentage is calculated on the dry dispersion).

The slurry can also conveniently be used as a storage medium for the microcapsules of the present disclosure. In case the microcapsules are stored in the form of aqueous based slurry but no water (or a limited amount of water) must be present in the final product, the slurry can be spray-dried and the spray-dried microcapsules are then added to the final intended product.

The present disclosure discloses a product comprising a microcapsule as defined above. The product may be a non-edible consumer goods product, a household cleaner or laundry product, a personal care product or a cosmetic product.

Conveniently, microcapsules presently disclosed and obtained using a blend including monomers (Ia), the product is liquid at room temperature and has a pH comprised between 2 and 12, for example more than 4 and less than 12.

Unless otherwise indicated, non-edible means non-intended for ingestion by humans or animals. This includes non-food products that may accidentally be swallowed during normal use. Notably, included within the definition of non-edible products are products for dental and oral care, such as toothpastes, mouth washes and lip balms which although not intended for ingestion may nevertheless accidentally enter the gastro-intestinal tract.

The formulations and ingredients of liquid household, laundry, personal care and cosmetic products in which microcapsules of the invention may be used are well known to those skilled in the art, reference may be made to the following works:

Formulating Detergents and Personal Care Products A guide to Product Development by L Ho Tan Tai, ISBN 1-893997-10-3 published by the AOCS Press Volume 67 of the Surfactant Science Series Liquid Detergents ISBN 0-8247-9391-9 (Marcel Dekker Inc), Harry's Cosmeticology published by CHS Press 8th Edn. 2000 ISBN 0820603724.

Personal care and cosmetic products may include products that can be applied to the skin, hair and nails either as leave on or rinse off product. Personal care and cosmetic products include powders, creams, emulsions, lotions, gels and oils for the skin (face, hands, feet etc), tinted bases (liquids and pastes) and liquid impregnated tissues; products for applying and removing make-up from the face and eyes; hair care products including hair tints and bleaches; products for waving, straightening, setting and fixing hair; shaving products including creams, foams mousses and depilatory products; sun bathing products and products for tanning without the sun; deodorant and antiperspirant products.

Advantageously a personal care or cosmetic product is selected from the group consisting of a shaving aid, a shampoo, a hair-conditioner product, a leave-on-skin-care product, a skin cleansing or washing product (such as a rinse-off skin cleansing or washing product), a moist tissue and a body spray, deodorant or antiperspirant.

Shaving aids specifically include foams, gels, creams and bars (reference can be made for example to U.S. Pat. No. 7,069,658, U.S. Pat. No. 6,944,952, U.S. Pat. No. 6,594,904, U.S. Pat. No. 6,182,365, U.S. Pat. No. 6,185,822, U.S. Pat. No. 6,298,558 and U.S. Pat. No. 5,113,585).

Shampoos and hair conditioners specifically include two-in-one shampoos and shampoos especially formulated for dry or greasy hair or containing additives such as antidandruff agents. Hair conditioners may be rinse off or leave on hair conditioners also included are hair tonics, bleaches colorants, setting and styling products. Reference can be made for example to U.S. Pat. No. 6,162,423, U.S. Pat. No. 5,968,286, U.S. Pat. No. 5,935,561, U.S. Pat. No. 5,932,203, U.S. Pat. No. 5,837,661, U.S. Pat. No. 5,776,443, U.S. Pat. No. 5,756,436, U.S. Pat. No. 5,661,118, U.S. Pat. No. 5,618,523.

Leave-on-skin-care products comprise skin washing products, moist tissues, body sprays, deodorants and antiperspirants.

Skin washing products specifically include beauty and hygiene bar soaps, shower gels, liquid soaps, body washes, exfoliating gels and pastes (reference can be made for example to U.S. Pat. No. 3,697,644; U.S. Pat. No. 4,065, 398; U.S. Pat. No. 4,387,040).

Moist tissues (wipes) specifically include skin cleansing wipes, baby wipes, make-up removal wipes and skin refreshing wipes (reference can be made for example to U.S. Pat. No. 4,775,582; WO02/07701; WO2007/069214 and WO95/16474).

Body sprays, deodorants and antiperspirants specifically include sticks, liquid roll-on applicators and pressurized sprays.

Examples of household cleaners and laundry products are:
hard surface cleaners such as cleaners for floors, solid work surfaces, tiled surfaces, crockery by hand or machine washing and mirrors and glass,
soft furnishing treatments such as liquid cleaners and refresher products such as odour treatment agents as exemplified by Febreze® (P&G),
powdered laundry detergents, detergent tablets and bars, laundry detergent liquids include light duty liquids, heavy duty liquids, concentrated liquid detergents, non or low aqueous laundry liquids and more specialised cleaners for woolen or dark garments,
fabric softeners and pre- and post-wash treatments such as tumble drier sheets, ironing waters and wash additives.

Advantageously, a laundry product is selected from the group consisting of a fabric softener, a fabric conditioner and a laundry detergent.

Household cleaners may be in the form of cream cleaners, isotropic liquid cleaners, spray cleaners and pre-moistened surface cleaning wipes (reference can be made for example to WO91/08283, EP743280, WO96/34938, WO01/23510, and WO99/28428).

Fabric softeners and conditioners specifically include both conventional diluted (e.g. 2% to 8% by weight of softener in the product) liquid active concentration softeners and concentrated (e.g. 10% to 40% by weight of softener in the product) liquid active concentration softeners as well as fabric conditioners which may contain ingredients to protect colors or garment shape and appearance (reference can be made for example to U.S. Pat. No. 6,335,315, U.S. Pat. No. 5,674,832, U.S. Pat. No. 5,759,990, U.S. Pat. No. 5,877,145, U.S. Pat. No. 5,574,179).

Laundry detergents, particularly liquid laundry detergents, specifically include light duty liquid detergents and heavy duty liquid detergents which may be structured multi-phase liquids or isotropic liquids and which may be aqueous or non-aqueous liquids. These liquids may be in bottles or unit dose sachets and they may optionally contain bleaching agents or enzymes (reference can be made for example to U.S. Pat. No. 5,929,022, U.S. Pat. No. 5,916,862, U.S. Pat. No. 5,731,278, U.S. Pat. No. 5,470,507, U.S. Pat. No. 5,466,802, U.S. Pat. No. 5,460,752, and U.S. Pat. No. 5,458,810).

The products presently disclosed may contain water and/or surface active material, either as an emulsifier, if the product is an emulsion, or as a detergent active material if the product has some kind of cleaning function. In certain embodiments the concentration of surface active material in the product will be within the range 0.1-60% by weight; usually the level of surface active material will be 50% by weight or lower; for most products the level of surface active material will be 30% by weight or lower. On the other hand, the level of surface active material will usually be at least 0.1% by weight preferably greater than 1.0% and more preferably greater than 3.0% by weight. Certain product formulations are water sensitive (e.g. anti-perspirant, deodorant formulations, non-aqueous liquids packaged in water soluble polyvinyl alcohol films), and for these applications it may be desirable to spray dry the microcapsules to remove water, before the microcapsules are incorporated in the product formulation. For products which have a cleaning function it is likely the level of surface active material will be higher, typically greater than 10% by weight and preferably greater than 15% by weight. All percentages are expressed by weight over the weight of the product.

Examples of leave-on products containing emulsifiers are: hand and body lotions, make up removing lotions, skin creams, sunscreen products and sunless tanning products and domestic freshener sprays. Also included are articles of manufacture impregnated with liquids, for example pads or wipes impregnated with lotions for make-up application or removal, or to apply sunscreen compounds or sunless tanning agents, for personal cleansing e.g. as moist toilet tissue or baby wipes.

Examples of personal cleansing products containing detergents are: shampoos, body washes, liquid soaps. Some cleaning products may be considered leave on products even though they are used for cleansing if there is no rinsing or further cleaning action after use. Baby wipes are an example, although used for cleaning the liquid deposited on the skin is not removed by rinsing.

The non-rinsed cosmetic, toiletry and personal care compositions described herein can contain various emulsifiers which are useful for emulsifying the various components of the products. Suitable emulsifiers can include any of a wide variety of non-ionic, cationic, anionic, and zwitterionic surface active materials as disclosed in publications such as McCutcheon's, Detergents and Emulsifiers, North American Edition (1986), published by Allured Publishing Corporation and in the following patents: U.S. Pat. No. 5,011,681; U.S. Pat. No. 4,421,769; and U.S. Pat. No. 3,755,560.

Experimental evidence shows that the composition of certain products such as setting lotions, eau de toilettes, body spray aerosols, hair foams, which contain short hydrocarbon chain alcohols may negate the benefit brought about by the microcapsules presently disclosed. Therefore, it is preferable that the products do not contain significant amounts (e.g. more than 2.5% or more than 5%, such as more than 10%, or more than 20% or more than 50% or more than 70% by weight over the weight of the product) of short hydrocarbon chain alcohols such as aliphatic $C_1$-$C_4$ alcohols (e.g. ethanol or isopropanol). Without wishing to be bound by any theory, it is believed that short hydrocarbon chain alcohols might affect the microcapsule integrity thereby facilitating the leakage of the perfume content.

Microcapsules amount into liquid household, laundry, personal care and cosmetic products may vary depending on several aspects such as the desired microcapsule concentration, the proportion of fragrance within the microcapsule and the amount of fragrance necessary to create the olfactory effect desired. After removing all liquid components from a given product (i.e. measured as dry weight) the microcapsules of the invention may be present from 0.01 to 10% by weight, preferably from 0.05% to 2.5% by weight, more preferably from 0.1 to 1.25% by weight over the weight of the product. The microcapsules may be incorporated into the products by any conventional means, usually as a water-based liquid dispersion added at a suitable stage in the product manufacturing process but usually after any high shear mixing stage. If liquid at room temperature, it is preferable that the product into which the microcapsules are to be added has a viscosity greater than 20 Mpas, for example greater than 100 Mpas, or greater than 1,000 Mpas, or even greater than 10,000 Mpas, when measured at a low (e.g. 10 rpm) spindle speed. Conveniently, the product shows shear thinning rheology. If necessary, viscosity can be adjusted through the addition of conventional viscosity modifying agents. Suitable agents as well as equipment and conditions to measure the viscosity of a product are discussed in Rheology Modifiers Handbook Practical Uses and Applications by M R Rosen and D Braun published by William Andrew Publishing in 2000 with ISBN 978-0-8155-1441-1.

Further embodiments and advantages of the present invention will become apparent to a skilled reader in light of the examples provided below.

Two alternatives for the General manufacturing process are disclosed. Alternative 1 is followed for monomer blends that do not comprise monomers with hydroxyl groups or monomers that are not solubilized in the fragrance. Alternative 2 is followed for monomer blends that comprise monomers with hydroxyl groups and/or monomers that are not solubilized in the fragrance. By "solubilized in the fragrance", it is meant that the amount of monomer considered is fully solubilized in the fragrance, forming a monophasic, homogeneous and transparent phase.

General Manufacturing Process—Alternative 1

A 10% poly(vinyl alcohol) aqueous solution was prepared in advance by dissolving poly(vinyl alcohol), hydrolyzed to 87-89%, $M_w$=85000-124000 g/mol in water. An oil phase was prepared by first mixing the fragrance and the monomers to obtain a monophasic, homogeneous and transparent phase. The polymerization initiator was then added and the mixture was stirred until complete dissolution of the polymerization initiator. A dispersion of silica in water was prepared separately by stirring during 5 min the Aerosil® R816 silica and the water with a pH between 6.5 and 8.5. The water dispersion contained sodium bicarbonate 100 mg/L (to approximately have a pH in the range of 6.5 to 8.5). The oil phase and the dispersion of silica in water were stirred together at 7000 rpm for 2 min using a high-shear mixer (Ystral X 10/20 E3-1050 W equipped with a Dispermix head of diameter 40/54 mm). The mean particle and the span number of the resultant emulsion were determined according to the capsule particle size measurement method disclosed below. The emulsion was placed into a batch reactor equipped with a condenser, a thermometer, a nitrogen inlet and an anchor stirrer. A known amount of 10% poly(vinyl alcohol) aqueous solution was added to get a total weight concentration of poly(vinyl alcohol) in the water phase of 2% and the mixture was stirred during 10 min. During all the process, the mixture was stirred at 250 rpm and nitrogen was bubbled through the mixture to remove oxygen. The temperature is first fixed at a temperature T1 during 30 min and the temperature is then increased to the temperature T2 within one hour. The mixture is kept at this temperature T2 during 3 hours. Finally, the resultant microcapsule dispersion was cooled to room temperature within 1 hour. The mean particle and the span number of the resultant microcapsule dispersion were determined according to the capsule particle size measurement method disclosed below.

General Manufacturing Process—Alternative 2

A 10% poly(vinyl alcohol) aqueous solution was prepared in advance by dissolving poly(vinyl alcohol), hydrolyzed to 87-89%, $M_w$=85000-124000 g/mol in water. An oil phase was prepared by mixing the fragrance and the monomers which are soluble in the fragrance except the monomer with hydroxyl groups. A monophasic, homogeneous and transparent phase was obtained. The polymerization initiator was then added and the mixture was stirred until complete dissolution of the polymerization initiator. This mixture was stirred until complete dissolution of the polymerization initiator. The water dispersion contained sodium bicarbonate 100 mg/L (to approximately have a pH in the range of 6.5 to 8.5). In water were introduced in the following order: the monomers with hydroxyl groups and/or the neutral monomers that are not soluble in the fragrance, a 1% solution of 3-(methacryloylamino)propyl]trimethylammonium chloride (MAPTAC) in water and the Aerosil® 200 silica. The weight of the 1% solution of MAPTAC in water represents between 0.5% and 100% of the weight of silica. The dispersion was stirred during 30 min. The water dispersion pH range was within a pH of 6.5 to 8.5. The oil phase and the dispersion of silica in water were stirred together at 7000 rpm for 2 min using a high-shear mixer (Ystral X 10/20 E3-1050 W equipped with a Dispermix head of diameter 40/54 mm). The mean particle and the span number of the resultant emulsion were determined according to the capsule particle size measurement method disclosed below. The emulsion was placed into a batch reactor equipped with a condenser, a thermometer, a nitrogen inlet and an anchor stirrer. A known amount of 10% poly(vinyl alcohol) aqueous solution was added to get a total weight concentration of poly(vinyl alcohol) in the water phase of 2.6% and the mixture was stirred during 10 min. If present, ionized monomers (which are not soluble in the fragrance) may be added at this stage. During all the process, the mixture was stirred at 250 rpm and nitrogen was bubbled through the mixture to remove oxygen. The temperature is first fixed at a temperature T1 during 30 min and the temperature is then increased to the temperature T2 within one hour. The mixture is kept at this temperature T2 during 3 hours. Finally, the resultant microcapsule dispersion was cooled to room temperature within 1 hour. The mean particle and the span number of the resultant microcapsule dispersion were determined according to the capsule particle size measurement method disclosed below.

Leakage Test Manufacturing Procedure

To evaluate the leakage associated to the choice of a specific crosslinker (compound (II)) as presently disclosed, the following manufacturing is followed. A 10% poly(vinyl alcohol) aqueous solution is prepared in advance by dissolving poly(vinyl alcohol), hydrolyzed to 87-89%, $M_w$=85000-124000 g/mol in water. An oil phase is prepared by mixing 150 g of fragrance no. 5, 21.8 g of methacrylic acid, 8.7 g of methyl methacrylate, 24.0 g of crosslinker, 2.5 g of 3-trimethoxysilyl propyl methacrylate, 1.5 g of lauroyl peroxide. The mixture is stirred in order to obtain a monophasic, homogeneous and transparent phase. The dispersion of silica in water is prepared separately by stirring during 5 min 1.25 g of Aerosil® R816 silica, 200 g of water containing 100 mg/L of sodium bicarbonate. The oil phase and the dispersion of silica in water are stirred together at 7000 rpm for 2 min using a high-shear mixer (Ystral X 10/20 E3-1050 W equipped with a Dispermix head of diameter 40/54 mm). If desired, the mean particle and the span number of the resultant emulsion are determined according to the capsule particle size measurement method disclosed below. 360 g of the emulsion are placed into a 500 mL-batch reactor equipped with a condenser, a thermometer, a nitrogen inlet and an anchor stirrer. 43 g of a 10% poly(vinyl alcohol) aqueous solution are added and the mixture is stirred during 10 min. During all the process, the mixture is stirred at 250 rpm and nitrogen is bubbled through the mixture to remove oxygen. The temperature is first fixed at a temperature of 25° C. during 30 min and the temperature is then increased to the temperature of 70° C. within one hour. The mixture is kept at 70° C. during 3 hours. Finally, the resultant microcapsule dispersion is cooled to room temperature within 1 hour. If desired, the mean particle and the span number of the resultant microcapsule dispersion are determined according to the capsule particle size measurement method disclosed below.

Fragrance Test Manufacturing Procedure

To identify particularly advantageous fragrances (or mixtures thereof), the following manufacturing procedure is followed. A 10% poly(vinyl alcohol) aqueous solution is prepared in advance by dissolving poly(vinyl alcohol), hydrolyzed to 87-89%, $M_w$=85000-124000 g/mol in water. An oil phase is prepared by mixing 150 g of the fragrance to test, 21.8 g of methacrylic acid, 8.7 g of methyl methacrylate, 24.0 g of 1,4-butane diol dimethacrylate, 1.5 g of benzoyl peroxide, 75% in water. The mixture is stirred in order to obtain a monophasic, homogeneous and transparent phase. A dispersion of silica in water is prepared separately by stirring during 5 min 1.25 g of Aerosil® R816 silica, 200 g of water containing 100 mg/L of sodium bicarbonate. The oil phase and the dispersion of silica in water are stirred together at 7000 rpm for 2 min using a high-shear mixer (e.g. Ystral X 10/20 E3-1050 W equipped with a Dispermix head of diameter 40/54 mm). The mean particle and the span number of the resultant emulsion are determined according to the capsule particle size measurement method disclosed below. 360 g of the emulsion are placed into a sealed 500 mL-batch reactor equipped with a condenser, a thermometer, a bottom outlet valve and an anchor stirrer. 43 g of 10% poly(vinyl alcohol) aqueous solution is added and the mixture is stirred during 10 min. During all the process, the mixture is stirred at 250 rpm. The temperature is first fixed at a temperature of 25° C. during 30 min and the temperature is then increased to the temperature of 80° C. within one hour. The mixture is kept at 80° C. and samples of 2 g are withdrawn by using the bottom outlet valve every 30 min in order to determine the monomer conversion according to the procedure defined below. The mixture is kept during a sufficient time at 80° C. to obtain a monomer conversion equal to 85% or higher than 85%. The resultant microcapsule dispersion is cooled to room temperature within 1 hour. The mean particle and the span number of the resultant microcapsule dispersion are determined according to the capsule particle size measurement method disclosed below.

The determination of the monomer conversion may be done through the following procedure. The samples withdrawn from the reactor are homogenized by stirring with a spatula. 150 mg of each sample are withdrawn and 20 mL of a 3% by weight 4-methoxyphenol solution in ethanol are added. The mixture is stirred and left in an ultrasonic bath for 30 minutes. The mixture is filtered on a 0.45 μm Acrodisc filter and the separated liquor is analyzed by GC/FID (gas chromatography equipped with a flame ionization detector). External calibration is performed with the solution of each monomer in ethanol. Integration areas are determined from the FID signal using Agilent® Chemstation software. Three replicate samples are extracted and analyzed. This analysis provides the weight of residual monomers in the sample. The monomer conversion is defined as:

$$\text{Monomer conversion (\%)} = \frac{\text{Initial weight of monomers} - \text{residual weight of monomers}}{\text{Initial weight of monomers}} \times 100$$

Solid Content Measurement Method

Approximately 3 g of slurry are weighted in an aluminum weighing dish and dried during two hours at 105° C. in order to remove water. The weight of the dry sample is then determined at room temperature and compared to the weight of the dispersion.

Capsule Particle Size Measurement

Median volume diameter and span were measured with a laser diffraction/scattering particle size distribution analyzer (trade name: LA-950V2, manufactured by Horiba, Ltd.). The dispersant was deionized water purified to 18 MΩ. Several droplets of the emulsion or the capsule dispersion were poured into the flow cell unit, an acceptable level of laser light obscuration was achieved and triplicate measurements were then immediately performed. For the calculation of the particle size measurement, the refractive indexes were set at 1.33 (for the water dispersant), 1.47 (for the fragrances and the poly(methacrylate) capsules). The median capsule diameter was measured as a particle size of 50% frequency (median size) on a volumetric basis.

The span was calculated according to the following formula:

$$\text{Span} = \frac{D(v; 0.9) - D(v; 0.1)}{D(v; 0.5)}$$

in which $D(v; 0.9)$ is the particle size for 90% of the microcapsules by volume, $D(v; 0.1)$ is the particle size for 10% of the microcapsules by volume and $D(v; 0.5)$ is the median volume microcapsule size as previously defined.

The Span ratio between the emulsion and the capsule dispersion was calculated according to the following formula:

$$\text{Span ratio} = \frac{\text{Span Capsule}}{\text{Span Emulsion}}$$

Wherein Span Capsule is the span as defined above of the microcapsule dispersion and the Span Emulsion is the span as defined above of the initial emulsion.

Since the particle size may be larger than 10 μm the analysis of the results by the Fraunhofer approximation (opaque particles, geometrical optic rules) is also relevant and lead to valid size determination. In this case the refractive index is not necessary.

Composition of Fragrances

Composition of Fragrance No. 1

| Ingredient | % (by weight) |
| --- | --- |
| Verdox (CAS No 88 41 5) | 19 |
| Isobornyl acetate (CAS No 125-12-2): | 19 |
| Undecalactone gamma (CAS No 104-67-6): | 10 |
| Camphor gum powder synthetic (CAS No 464-49-3): | 10 |
| 2-methyl undecanal (CAS: 110-41-8) | 10 |
| Cyclacet (CAS No 54830-99-8): | 10 |
| Iso E super (CAS No 54464-57-2 166090-45-5) | 10 |
| Allyl heptoate (CAS No 142-19-8): | 10 |
| Delta damascone (CAS No 57378-68-4): | 2 |

Composition of Fragrance No. 2

| Ingredient | % (by weight) |
| --- | --- |
| Verdox (CAS No 88 41 5) | 20 |
| Isobornyl acetate (CAS No 125-12-2) | 20 |
| Undecalactone gamma (CAS No 104-67-6) | 10 |
| Camphor gum powder synthetic (CAS No 464-49-3) | 10 |
| 2-methyl undecanal (CAS: 110-41-8) | 10 |
| Linalool (CAS No 78-70-6) | 10 |
| Linalyl acetate (CAS: 115-95-7) | 5 |
| Pinene beta (CAS No 127-91-3) | 5 |
| Citral (CAS No 5392-40-5) | 5 |
| Levosandol (CAS: 28219-61-6) | 5 |

Composition of Fragrance No. 3

| Ingredient | % (by weight) |
| --- | --- |
| Verdox (CAS No 88 41 5) | 21 |
| Isobornyl acetate (CAS No 125-12-2): | 21 |
| Dihydromyrcenol (CAS: 18479-58-8) | 20 |
| Undecalactone gamma (CAS No 104-67-6): | 10 |
| Camphor gum powder synthetic (CAS No 464-49-3): | 10 |
| 2-methyl undecanal (CAS: 110-41-8) | 10 |
| Geraniol (CAS: 106-24-1) | 5 |
| Patchouli oil de-ironized natural (supplier: Reynaud ™, CAS: 84238-39-1) | 1 |
| (E,Z)-2,6-nonadien-1-ol (CAS: 28069-72-9) | 0.5 |
| Damascenone (CAS: 23726-93-4) | 0.5 |
| Isofreshal (CAS: 68259-31-4) | 0.5 |
| Vanitrope (CAS: 94-86-0) | 0.5 |

Composition of Fragrance No. 4

| Ingredient | % (by weight) |
| --- | --- |
| Verdox (CAS No 88 41 5) | 26.4 |
| Floropal (CAS: 5182-36-5) | 10 |
| Ethyl caproate (CAS: 123-66-0) | 6 |
| Benzyl salicylate (CAS: 118-58-1) | 5 |
| Nerolin Bromelia (CAS: 93-18-5) | 5 |
| Triplal (CAS: 27939-60-2) | 5 |
| Lilial (CAS: 80-54-6) | 5 |
| para-Mentha-8-thiol-3-one (CAS: 38462-22-5), 1% in isopropylmyristate | 5 |
| Allyl caproate (CAS: 123-68-2) | 5 |
| Ethyl butyrate (CAS: 105-54-4) | 4 |
| Ethyl 2-methylbutyrate (CAS: 7452-79-1) | 3 |
| Ethyl 2-methylpentanoate (CAS: 39255-32-8) | 3 |
| Fruitate (CAS: 80623-07-0, 80657-64-3) | 3 |
| 2-Methyl-1,3-dioxolane (CAS: 497-26-7) | 3 |
| Diphenyl oxide(CAS: 101-84-8) | 2.5 |
| Isocyclocitral (CAS: 1335-66-6) | 2.5 |

-continued

| Ingredient | % (by weight) |
|---|---|
| Camphor gum powder synthetic (CAS No 464-49-3): | 2 |
| Delta damascone (CAS No 57378-68-4): | 2 |
| Eucalyptol (CAS: 470-82-6) | 2 |
| Galbascone BHT (CAS: 56973-85-4, 128-37-0) (Supplier: IFF) | 0.2 |
| para- menth-1-ene-8-thiol (CAS: 71159-90-5), 1% in triethyl citrate | 0.2 |
| Ambretone (CAS: 37609-25-9) | 0.1 |
| Karanal (CAS: 117933-89-8) | 0.1 |

Composition of Fragrance No. 5

| Ingredient | % (by weight) |
|---|---|
| Isobornyl acetate (CAS No 125-12-2): | 25 |
| Camphor gum powder synthetic (CAS No 464-49-3): | 15 |
| Lilial (CAS No 80-54-6): | 15 |
| Eucalyptol (CAS No 470-82-6): | 8 |
| Ethyl-2-methylpentanoate (CAS No 39255-32-8): | 6 |
| Cedrol (CAS No 77-53-2): | 6 |
| Allyl heptoate (CAS No 142-19-8): | 5 |
| Styrallyl acetate (CAS No 93-92-5): | 5 |
| 2-Methylundecanal (CAS No 110-41-8): | 5 |
| Verdox (CAS: 88-41-5): | 5 |
| Coumarin (CAS No 91-64-5): | 3 |
| Delta damascone (CAS No 57378-68-4): | 2 |

The fragrance no. 5 is the fragrance to be used in the leakage test method.

Example 1: Synthesis of the Capsules According to the Invention

The general manufacturing process was followed for to prepare microcapsule samples 1 to 6 wherein the monomer blend did include a silane monomer (III). The exact conditions of synthesis and the results of characterization are given in the Table below. The span ratio between the emulsion and the capsule dispersion for these samples 1 to 6 are all below 1.25, indicating that the presence of the 3-trimethoxysilyl propyl methacrylate prevents the formation of latex particles in the aqueous phase.

Example 2 (Comparative)

The procedure disclosed in Example 1 was followed to prepare microcapsule samples 7 to 10 wherein the monomer blend did not include a silane monomer (III). The mean particle and the span number of the resultant microcapsule dispersion were determined according to the capsule particle size measurement method disclosed below. The span ratio between the emulsion and the capsule dispersion for these samples 7 to 10 are all above 1.4.

Monomer Abbreviations:
MA: methacrylic acid
HEMA: 2-hydroxyethyl methacrylate
MMA: methyl methacrylate
BDMA: 1,4-butanediol dimethacrylate
TMPS: 3-trimethoxysilyl propyl methacrylate

| (A) | (B) | (C) | (D) | (E) | (F) | (G) | (H) | (I) | (L) | (M) |
|---|---|---|---|---|---|---|---|---|---|---|
| 1 | 1 | 36.6 | 2.63 | MA: 39<br>MMA: 15<br>BDMA: 41<br>TMPS: 5 | 177 | Benzoyl peroxide 75% | 45.1 | 20/80 | 38.9 | 1.13 |
| 2 | 2 | 36.6 | 2.63 | MA: 39<br>MMA: 15<br>BDMA: 41<br>TMPS: 5 | 177 | Lauroyl peroxide 97% | 38.0 | 20/70 | 42.3 | 1.17 |
| 3 | 3 | 36.6 | 2.63 | MA: 39<br>MMA: 15<br>BDMA: 41<br>TMPS: 5 | 177 | Lauroyl peroxide 97% | 38.0 | 20/70 | 44.3 | 1.23 |
| 4 | 4 | 36.6 | 2.63 | MA: 39<br>MMA: 15<br>BDMA: 41<br>TMPS: 5 | 177 | Lauroyl peroxide 97% | 38.0 | 20/70 | 39.1 | 1.17 |
| 5 | 5 | 36.6 | 2.63 | MA: 39<br>MMA: 15<br>BDMA: 41<br>TMPS: 5 | 177 | Lauroyl peroxide 97% | 38.0 | 20/70 | 39.8 | 1.10 |
| 6 | 5 | 39.0 | 2.69 | HEMA: 43<br>BDMA: 52<br>TMPS: 5 | 149 | Benzoyl peroxide 75% | 45.1 | 35/80 | 37.6 | 1.15 |
| 7 | 1 | 36.7 | 2.75 | MA: 40<br>MMA: 16<br>BDMA: 44 | 180 | Benzoyl peroxide 75% | 44.3 | 20/80 | 49.4 | 3.05 |
| 8 | 2 | 36.8 | 2.75 | MA: 40<br>MMA: 16<br>BDMA: 44 | 172 | Lauroyl peroxide 97% | 35.4 | 20/70 | 41.8 | 1.44 |
| 9 | 3 | 36.8 | 2.75 | MA: 40<br>MMA: 16<br>BDMA: 44 | 172 | Lauroyl peroxide 97% | 35.4 | 20/70 | 60.9 | 1.75 |

-continued

| (A) | (B) | (C) | (D) | (E) | (F) | (G) | (H) | (I) | (L) | (M) |
|---|---|---|---|---|---|---|---|---|---|---|
| 10 | 4 | 36.8 | 2.75 | MA: 40<br>MMA: 16<br>BDMA: 44 | 172 | Lauroyl peroxide 97% | 35.4 | 20/70 | 60.9 | 1.75 |

(A) Sample #
(B) Fragrance #
(C) Weight concentration of fragrance in the emulsion
(D) Fragrance/monomers weight ratio in the emulsion
(E) Composition of the blend (% represents the amount by weight of each monomer over the combined weight of all monomers in the blend) wherein:
MA: methacrylic acid
MMA: methyl methacrylate
BDMA: 1,4-butanediol dimethacrylate
TMPS: 3-trimethoxysilyl propyl methacrylate
HEMA: 2-hydroxyethyl methacrylate
(F) Oil phase/silica particles weight ratio
(G) Polymerization initiator (% represents the weight concentration of initiator in the commercially available product)
(H) Monomer/initiator weight ratio
(I) T1/T2 (° C.)
(L) Median volume diameter of the capsule dispersion (μm; D(v, 0.5))
(M) Span ratio

Example 3—Viscosity Measurements

The viscosity measurement of the capsules dispersions were performed at 20° C. using a Brookfiel viscosimeter model DV-I, spindle 18. Depending on the viscosity of the capsules dispersions, the measurements were performed with adapted rotational spindle speeds.

Results:

| Sample | Viscosity at 20° C. (cps) | Spindle speed (rpm) |
|---|---|---|
| 1 | 100 | 12 |
| 2 | 370 | 6 |
| 3 | 390 | 6 |
| 4 | 170 | 12 |
| 5 | 190 | 12 |
| 6 | 1000 | 2.5 |
| 7 | 70 | 20 |
| 8 | Very viscous, as a paste (viscosity cannot be measured) | / |
| 9 | 120 | 12 |
| 10 | Very viscous, as a paste (viscosity cannot be measured) | / |

These results show that in absence of TMPS, a very viscous capsule dispersion may be obtained (Samples 8 and 10) whereas the viscosity is decreased for the corresponding capsule dispersions synthesized in presence of TMPS (Samples 2 and 4).

Example 4: Determination of the Fragrance Leakage (Leakage Test Method)

A mixture containing 0.5% w/w of the synthesized capsule dispersion and 99.5% w/w of a test liquid base is stored in a glass bottle in an oven at the controlled temperature of 40° C. for 1/2/4/6 weeks. After each time of storage, the mixture is shaken and 10 g are withdrawn. This sample is centrifuged to separate the fabric softener from the capsules. 1 g of centrifuged fabric softener is mixed with 1 g of celite (diatomaceous earth). 545.5 mL of pentane and 50 μL of an internal standard solution (see below for composition) are added. The mixture is agitated on a roller bed for 1 hour. The supernatant is then injected in GC/FID (gas chromatography apparatus using a flame ionization detector). Integration areas are determined from the FID signal using Agilent® Chemstation software. Each extract is analyzed three times. The internal standard solution is a solution of methyl decanoate in hexane at a concentration of 10 mg/mL.

Instrumentation:

Agilent 6890 GC connected to Chemstation software

Column: HP-5MS, 30 m×0.25 mm×0.25 μm

Oven temperature: 50° C. for 2 min then heat to 280° C. at 10° C./min and hold at 280° C. for 5 min.

Injector: 250° C., Detector: 250° C.

2 μL injection volume (splitless)

Calculations:

Determination of the weight of leaked fragrance component i in the sample:

$$W_{perf,i} = \frac{A_{perf,i} \times w_{IS}}{A_{IS}}$$

$W_{perf,i}$: weight of leaked fragrance component i (mg)
$A_{perf,i}$: fragrance component i area
$w_{IS}$: weight of internal standard (mg)
$A_{IS}$: internal standard area Determination of the weight of leaked fragrance in the sample:

$$W_{frag} = \sum_i W_{perf,i}$$

$W_{frag}$: weight of leaked fragrance (mg)

Determination of the percentage of the fragrance leakage:

$$\% \text{ leakage}_{frag} = \frac{W_{frag}}{W_{tot\ frag}} \times 100$$

% leakage$_{frag}$: percentage of fragrance leakage
$W_{tot\ frag}$: weight of encapsulated fragrance in the capsule dispersion determined experimentally Determination of the percentage of leakage of fragrance component i:

$$\% \text{ leakage}_{perf} = \frac{W_{perf}}{W_{tot\ perf.}} \times 100$$

% leakage$_{perf}$: percentage of leakage of fragrance component i.

$W_{tot\ perf}$: weight of encapsulated fragrance component i in the capsule dispersion determined experimentally.

The above procedure for measuring leakage was run using the commercial fabric softener Le Chat 0% (France) as test liquid base. Results were as follows:

| Period of storage (weeks) | Leakage of the encapsulated fragrance (% fragrance leakage) | | |
|---|---|---|---|
| | 0 | 1 | 4 |
| Sample 1 | 1.7 | 11.3 | 17.1 |
| Sample 2 | 5.2 | 25.2 | 28.0 |
| Sample 7 | 1.4 | 38.0 | 41.9 |
| Sample 8 | 1.9 | 39.2 | 43.8 |

These results show that the use of TMPs also allows to decrease the fragrance leakage from the capsule along the time of storage in the liquid medium (see results of sample 1 in comparison to sample 7, and results of sample 2 in comparison to sample 8).

When wanting to rely on the protocol of Example 4 as general procedure to test fragrance leakage of the microcapsules presently disclosed, the following test liquid base is used:

| | |
|---|---|
| Praepagen ® TQ 90% | 20.00% by weight |
| Deionised water | 79.87% by weight |
| Magnesium chloride hexahydrate 99% | 0.13% by weight |
| Citric acid | till achieving pH of 2.5. |

Praepagen® TQ 90% is triethanolamine dialkylester methosulphate in isopropanol, CAS 91995-81-2.

This application is based on European Patent Application No. 13306093.9 filed on Jul. 29, 2013, the entire subject matters of which are incorporated herein by reference. In addition, the subject matters of all documents cited in the specification are also incorporated here by reference.

INDUSTRIAL APPLICABILITY

The microcapsule containing one or more fragrances is suitable for inclusion in non-edible consumer goods products, laundry products, personal care products and cosmetic products. The microcapsule can be obtained in an economic and efficient manner by polymerizing an emulsion so that emulsion droplets are encapsulated into a subsequently cured polymeric shell.

The invention claimed is:

1. A microcapsule comprising a perfume composition enclosed within a polymeric shell, wherein:
    the perfume composition includes a fragrance,
    the polymeric shell includes solid colloidal particles having an average primary particle size comprised between 5 nm and 1 μm,
    the polymeric shell further includes in polymerized form a blend including:
    i) between 20% and 75% by weight over the combined weight of compounds (I) to (III) in the blend of a compound (I) which is a monoethylenically unsaturated monomer and/or dimethyldiallyl ammonium chloride,
    ii) between 20% and 70% by weight over the combined weight of compounds (I) to (III) in the blend of a compound (II) which is a polyethylenically unsaturated monomer selected from the group consisting of a $C_2$-$C_{24}$ alkyl di- or polyester of (meth)acrylic acid, a $C_2$-$C_{24}$ alkyl di- or polyamide of (meth)acrylic acid and mixtures thereof, and
    iii) between 0.01% and 10% by weight over the combined weight of compounds (I) to (III) in the blend of a compound (III) which comprises methacryloxypropyltrimethoxysilane and/or methacryloxypropyltriethoxysilane; and
    wherein the microcapsule has a shell thickness of 100 nm to 800 nm, and
    the microcapsule has an average particle size of 20 μm or more.

2. The microcapsule according to claim 1, wherein the compound (II) is such that the microcapsule provides for a fragrance leakage of less than about 35% when tested upon storage for 4 weeks at 40° C. in a test liquid base, according to a leakage test method, when the microcapsule is prepared according to a leakage test manufacturing procedure, and the microcapsule encapsulates fragrance no. 5, the test liquid base, the leakage test method, the leakage test manufacturing procedure and the fragrance no. 5 being as defined in the examples.

3. The microcapsule according to claim 1, wherein the compound (II):
    A1. contains two or more (meth)acrylate ester groups or two or more (meth)acrylate amide groups per monomer, and
    B1. has a molecular weight which, once divided by the number of (meth)acrylate ester or amide groups, gives a value of more than 85 and lower than 135.

4. The microcapsule according to claim 1, wherein the compound (I) is selected from the group consisting of methacrylic acid, methyl methacrylate, ethyl methacrylate, isopropyl methacrylate, 2-hydroxyethyl methacrylate, 2-hydroxypropyl methacrylate, 3-hydroxypropyl methacrylate and mixtures thereof.

5. The microcapsule according to claim 1, wherein the compound (I) is a combination of:
    ia) between 50% and 100% by weight over the weight of the combination of a neutral monomethacrylate monomer (Ia) having a solubility in water at pH 7 and 20° C. equal to, or more than 2 g/100 ml,
    ib) between 0% and 50% by weight over the weight of the combination of another neutral monoethylenically unsaturated monomer (Ib), and
    ic) between 0% and 15% by weight over the weight of the combination of an ionized or ionizable monoethylenically unsaturated monomer (Ic).

6. The microcapsule according to claim 5, wherein the neutral monomethacrylate monomer (Ia) is selected from the group consisting of 2-hydroxyethyl methacrylate, 2-hydroxypropyl methacrylate, 3-hydroxypropyl methacrylate, glycidyl methacrylate, poly(ethylene glycol) methyl ether methacrylate and mixtures thereof.

7. The microcapsule according to claim 1, wherein the compound (II) is a di- or polyester resulting from the esterification of (meth)acrylic acid with a linear or branched polyhydric $C_2$-$C_{24}$ alcohol and/or $C_2$-$C_{24}$ polyethylene glycols.

8. The microcapsule according to claim 7, wherein the compound (II) comprises one or more of 1,4-butylene glycol dimethacrylate, ethylene glycol dimethacrylate and 1,3-propylene glycol dimethacrylate.

9. A water-based dispersion comprising the microcapsule as defined according to claim 1.

10. The water-based dispersion according to claim 9, which is substantially free of latex particles.

11. A product comprising the microcapsule as defined according to claim 1, and which is a non-edible consumer goods product, a household cleaner or laundry product, a personal care product or a cosmetic product.

12. A process for the manufacture of the microcapsule as defined in claim 1, which comprises the following steps:
 a) providing an oil-in-water emulsion having an oil phase and a water phase, said oil-in-water emulsion being obtainable by mixing:
  colloidal silica particles having an average primary particle size comprised between 5 nm and 1 μm,
  an oil soluble polymerization initiator,
  a perfume composition including a fragrance,
  the blend as defined by claim 1, and
  a protective colloid,
 b) triggering polymerization within the oil phase of the oil-in-water emulsion obtained in step a),
 c) letting the polymerization propagate thereby obtaining microcapsules.

13. The microcapsule according to claim 1, wherein compound (III) is present between 0.5 and 10% by weight over the combined weight of compounds (I) and (III).

14. The microcapsule according to claim 1, wherein compound (III) is present between 0.5 and 5% by weight over the combined weight of compounds (I) to (III).

15. The microcapsule according to claim 1, wherein compound (III) is present between 1 and 5% by weight over the combined weight of compounds (I) to (III).

16. The microcapsule according to claim 1, wherein the microcapsule has a shell thickness of 200 nm to 700 nm.

17. The microcapsule according to claim 1, wherein the microcapsule has a shell thickness of 300 nm to 600 nm.

18. The microcapsule according to claim 1, wherein the microcapsule has an average particle size of 25 μm or more.

* * * * *